US012290324B2

(12) United States Patent
Bloomfield et al.

(10) Patent No.: US 12,290,324 B2
(45) Date of Patent: May 6, 2025

(54) TRACKER MOUNTING APPARATUS WITH KINEMATIC INTERFACES

(71) Applicant: INTELLIJOINT SURGICAL INC., Kitchener (CA)

(72) Inventors: Riley Aaron Bloomfield, New Hamburg (CA); Joseph Arthur Schipper, Kitchener (CA); Andre Novomir Hladio, Waterloo (CA)

(73) Assignee: Intellijoint Surgical Inc., Kitchener (CA)

( * ) Notice: Subject to any disclaimer, the term of this patent is extended or adjusted under 35 U.S.C. 154(b) by 156 days.

(21) Appl. No.: 18/098,315

(22) Filed: Jan. 18, 2023

(65) Prior Publication Data

US 2023/0233265 A1 Jul. 27, 2023

Related U.S. Application Data

(60) Provisional application No. 63/302,680, filed on Jan. 25, 2022.

(51) Int. Cl.
*A61B 34/20* (2016.01)
(52) U.S. Cl.
CPC ...... *A61B 34/20* (2016.02); *A61B 2034/2046* (2016.02)
(58) Field of Classification Search
None
See application file for complete search history.

(56) References Cited

U.S. PATENT DOCUMENTS

| 2005/0119639 | A1* | 6/2005 | McCombs | A61B 34/20 606/1 |
| 2017/0119478 | A1* | 5/2017 | Malackowski | A61B 34/30 |
| 2018/0296278 | A1* | 10/2018 | Van Beek | A61B 17/7076 |
| 2019/0209080 | A1* | 7/2019 | Gullotti | A61B 17/7035 |
| 2020/0368898 | A1* | 11/2020 | Perez | B25J 9/0039 |
| 2021/0369353 | A1* | 12/2021 | Nikou | A61B 90/39 |

* cited by examiner

Primary Examiner — Joel Lamprecht
Assistant Examiner — Ashish S Jasani

(57) ABSTRACT

There are provided tracker coupling apparatus for coupling an optical tracker to a patient anatomy. An apparatus comprises a body having a bone coupling interface located at a first end of the body, for coupling the apparatus to the bone, and a second end that comprises a tracker coupling interface to couple to the tracker. The second end is connected to the first end by an extension member to laterally space the tracker coupling interface from the bone coupling interface, e.g. to move the tracker away from an incision. In a resection guided embodiment, an apparatus comprises a body having a tracker coupling interface on an upper surface and a plurality of bone engaging projections extending from an under surface. Some projections are configured for positioning the platform in a same repeatable mounting position. The mounting position is defined by a cut line and an impression defined by the platform.

21 Claims, 17 Drawing Sheets

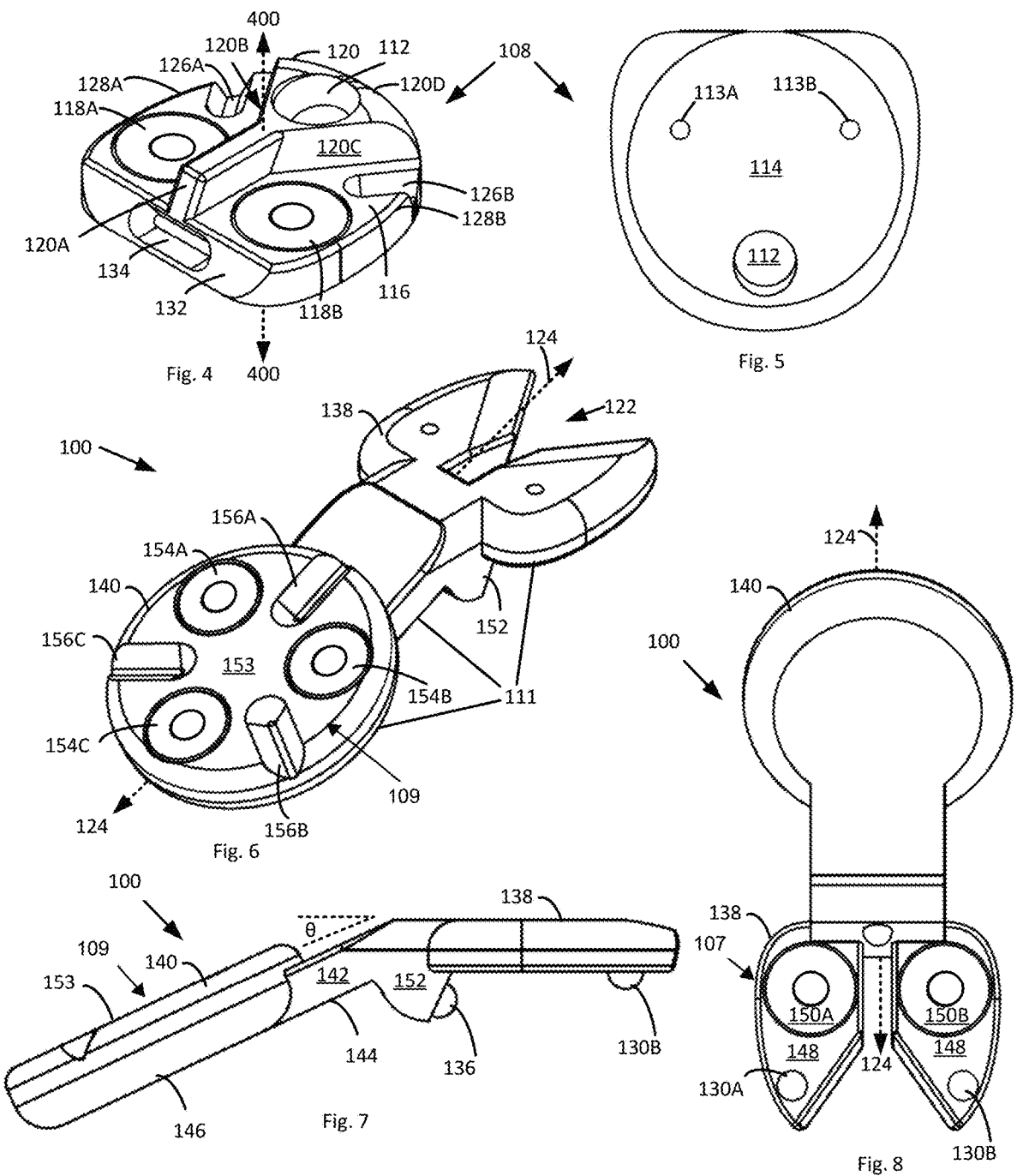

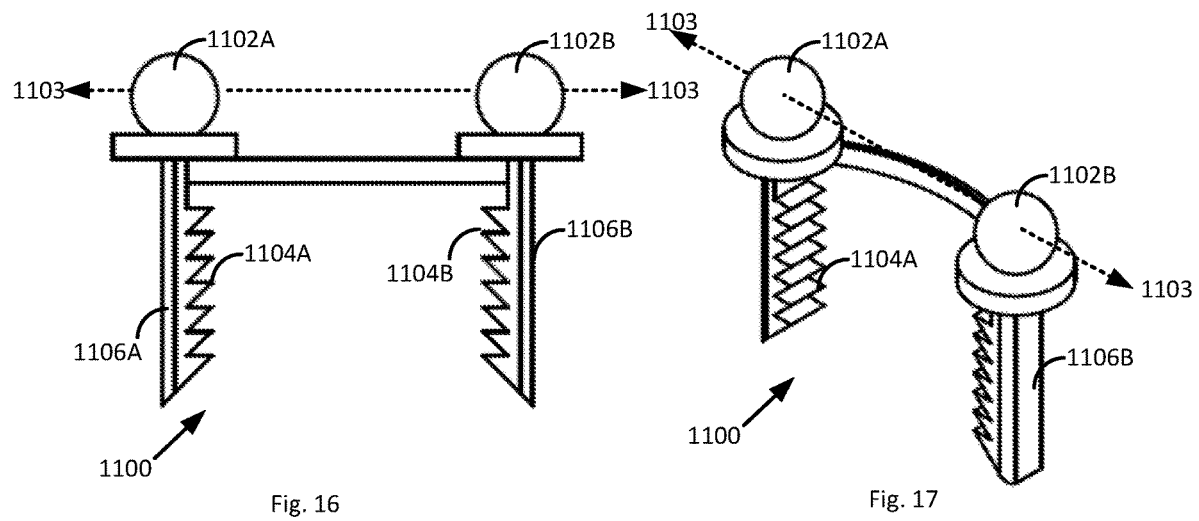
Fig. 16
Fig. 17
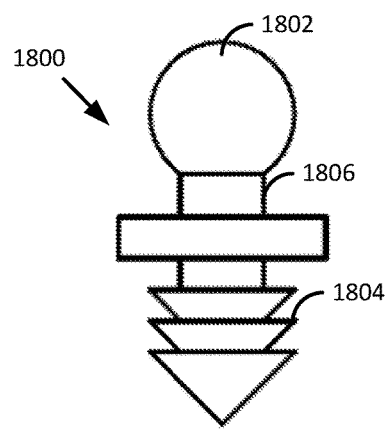
Fig. 18
Fig. 19

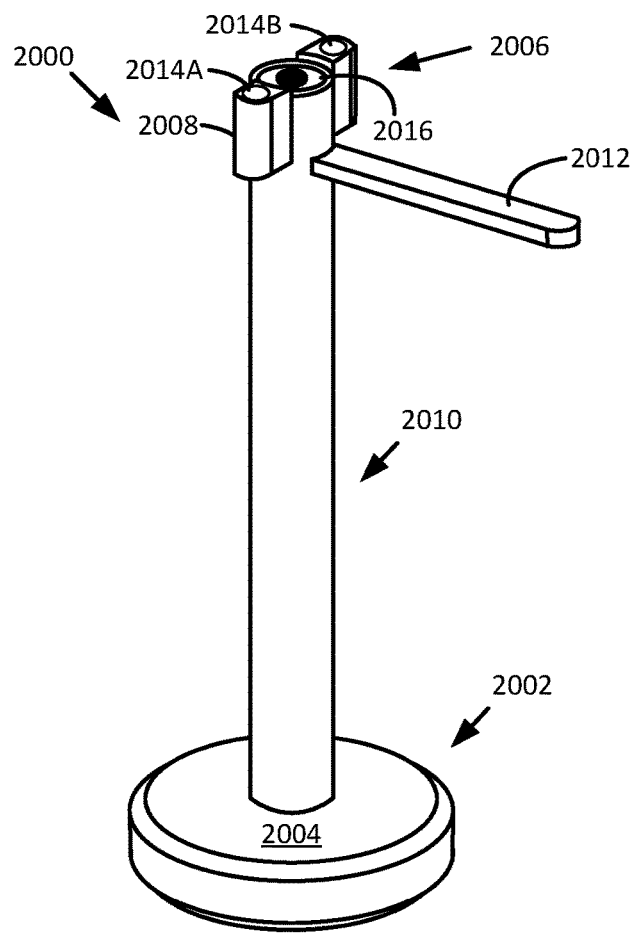
Fig. 22
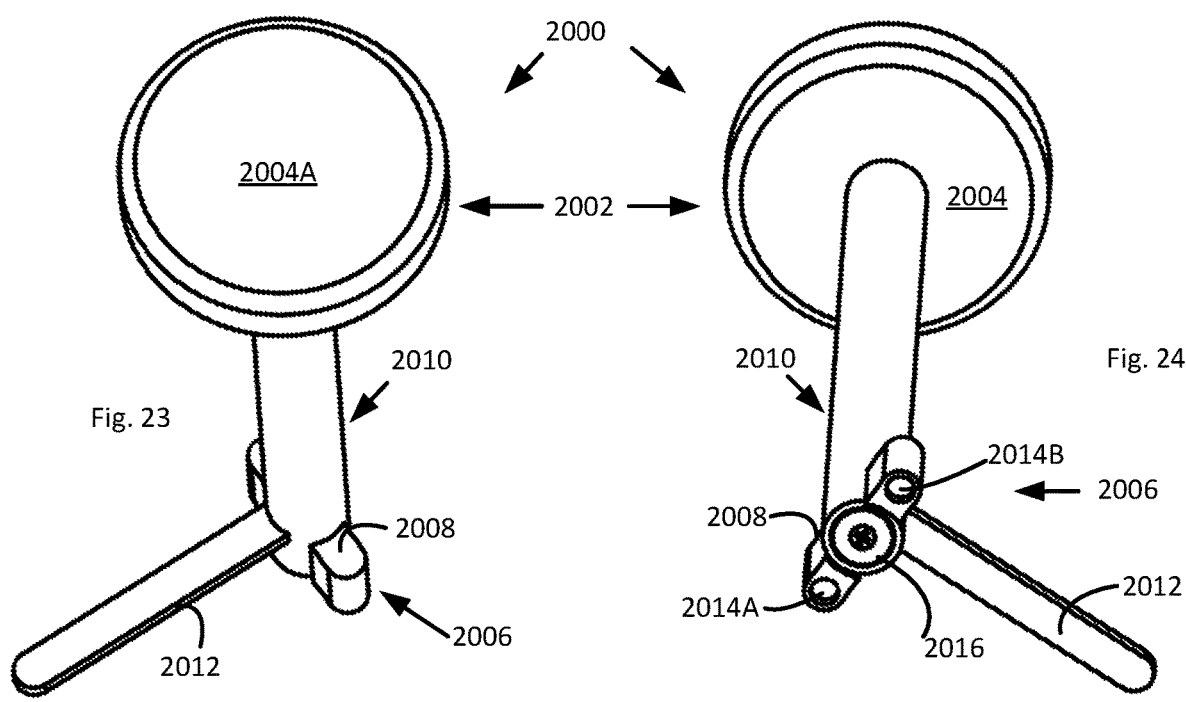
Fig. 23
Fig. 24

3500 

Registering a bone to a localization system, the localization system in communication with a tracker assembly comprising a tracker coupled to a resection guided platform coupled to the bone to simultaneously engage: i) a cut engaging projection of the platform to a preparatory cut; and ii) a marker projection of the platform in an impression in a second portion of the bone; wherein each of a) the impression and the preparatory cut; and b) the impression and the final cut; defining a same repeatable mounting position for the resection guided platform

3502

Receiving tracking information at the localization system from the tracker assembly when the tracker is coupled to the resection guided platform and the platform is in the same repeatable mounting position

3504

Generating and presenting at least one of guidance and a measurement generated from the registration and the tracker information

TRACKER MOUNTING APPARATUS WITH KINEMATIC INTERFACES

CROSS-REFERENCE

This application claims a benefit of U.S. Provisional Application No. 63/302,680, filed Jan. 25, 2022, the entire contents of which are incorporated herein by reference.

FIELD

This disclosure relates to surgical apparatus such as for a localization system for computer-assisted surgery, and more particularly to tracker mounting apparatus with kinematic interfaces for mounting an optical tracker to a patient anatomy.

BACKGROUND

Computer-assisted surgery seeks to enhance patient outcomes by providing clinically relevant measurement information and guidance. Localization systems track objects in a three dimensional (3D) space, which in a surgical context is an operating room. A tracking device, for example an optical tracker, can be coupled to an object, such as a bone, a tool or an implant and tracked using a localization system camera. A tracker mounting apparatus provides an interface to securely couple a tracker to the object. Camera data is useful to determine the position of the object in the field of view of the camera in the operating room. Through registration procedures, for example, a relative position of an object to another object or to a patient image or model can be determined. Localization information, including relative position information, can be displayed to provide clinically relevant measurements, and can be used to guide the surgical procedure.

Bones, particularly femurs, are often tracked in the context of hip and knee surgeries. Incisions that expose a bone surface for surgery are often kept to a minimum to reduce invasion. In at least some approaches, including an anterior approach in total hip arthroplasty (THA), the exposed portions of bone surfaces of the proximal femur provide contoured surfaces and/or a relatively small area for receiving a mounting apparatus. It is often desirable to mount a tracker in a manner that avoids expanding the size of the incision and crowding the neck area of the femur to improve line of sight and access to the area, for example, for resection, etc. It can also be desirable to provide a mounting apparatus that provides a quick connect mechanism to facilitate accurate placement, removal and replacement on the mounting apparatus to permit selective use of the tracker during phases of the surgical intervention.

It is desired to provide a tracker mounting apparatus to mount a tracker to a bone surface.

SUMMARY

There is provided tracker coupling apparatus for coupling an optical tracker to a patient anatomy. In an embodiment, the apparatus comprises a body having a bone coupling interface located at a first end of the body, for coupling the apparatus to the bone, and a second end that comprises a tracker coupling interface to couple to the tracker where the second end is connected to the first end by an extension member to laterally or anteriorly space the bone coupling interface and the tracker coupling interface. In an embodiment, there is a resection guided platform comprising a body having a tracker coupling interface on an upper surface and a plurality of bone engaging projections extending from an under surface that are configured for positioning the platform in a same repeatable mounting position defined by a cut line and an impression defined by the platform.

There is provided a side mount platform to mount a tracker to a bone via a coupling base, the platform comprising: a body having a first end member and a second end member laterally connected to and spaced from the first end member by an extension member of the body; wherein the first end member comprises an under surface providing a base coupling interface for coupling to the coupling base; and wherein the second end member comprises an upper surface providing a tracker coupling interface for coupling the platform to the tracker.

In an embodiment, the extension member is angled such that a plane occupied by an upper surface of the first end member is different from a plane occupied by the upper surface of the second end member. In an embodiment, an under surface of the extension member and an under surface of the second end are configured to follow a contour along a portion of the bone over which the extension member and the second end are to be placed.

In an embodiment, the tracker coupling interface comprises a cooperative interface for coupling to a quick connect mechanism of the tracker.

In an embodiment, the tracker coupling interface is magnetic.

In an embodiment, the first end defines at least one recess for the base coupling interface to receive a portion of the coupling base.

In an embodiment, the first end defines at least one projection for base coupling interface to fit a cooperating recess of the coupling base.

In an embodiment, the first end defines a recess for the base coupling interface to receive a cooperating projection of the coupling base for guiding a lateral coupling of the platform and coupling base. In an embodiment, the recess is Y-shaped.

In an embodiment, the base coupling interface comprises at least one magnet to couple with the coupling base. In an embodiment, each of the at least one magnet is positioned on the first end to mate with a cooperating magnet of the coupling base.

In an embodiment, the base coupling interface constrains movement of the platform in 6 degrees of freedom when coupled to the coupling base.

In an embodiment, the base coupling interface constrains movement of the platform in 5 degrees of freedom when coupled to the coupling base, the base coupling interface permitting rotation of the platform about an axis of the coupling base. In an embodiment, the base coupling interface comprises a pair of magnets coupled with a ferrous coupler, the magnets deposed over a pair of recesses configured to receive spherical projections of the coupling base. In an embodiment, one of the pair of recesses comprises a socket and the other a channel. In an embodiment, an under surface of the second end comprises a bone engaging projection, which projection, when a force is applied to the upper surface of the second end, engages a portion of the bone to stop rotation about the axis.

In an embodiment, the platform is a component of an assembly comprising the coupling base. In an embodiment, the coupling base comprises a base body having a bone engaging surface and an opposing surface; the opposing surface providing a cooperative interface to engage the bone coupling interface of the platform. In an embodiment, the base body defines an aperture therethrough extending between the opposing surface and the bone engaging surface to receive a fastener for coupling the base body to a coupling portion of the bone. In an embodiment, the aperture is angled from normal to direct the fastener.

In an embodiment, the coupling base comprises one of: a staple and a pair of pegs. In an embodiment, each of the staple and the pair of pegs comprises a pair of spherical tips to engage a pair of recesses of the base coupling interface in the under surface of the first end.

In an embodiment, there is provided a method comprising: coupling a coupling base to a first portion of a bone as exposed; coupling a side mount platform to the coupling base via a base coupling interface of a first end member of the platform, the platform comprising body having the first end member and a second end member laterally connected to and spaced from the first end by an extension member of the body; and coupling a tracker coupling interface of the second end member to a tracker.

In an embodiment, the method comprises, prior to coupling the coupling base to the first portion of the bone, performing an incision through soft tissue adjacent to the first portion of the bone; retracting the soft tissue to expose the first portion for coupling the coupling base; and at least partially releasing the soft tissue, wherein when coupled, the first end member is positioned away from the incision.

In an embodiment, the method comprises: performing a registration operation to register the bone to a localization system with the tracker assembled to the platform; removing the tracker from the platform; replacing the tracker on the platform; and receiving from the localization system at least one of guidance and a measurement using information from the tracker, the at least one of the guidance and the measurement generated without performing a subsequent registration operation.

It is understood that in the method embodiment, the coupling base and side mount platform can have any applicable the features thereof from their respective embodiments. These and other aspects will be apparent to those of skill in the art.

BRIEF DESCRIPTION OF THE DRAWINGS

FIG. 4 is top perspective view of the base of FIG. 1 in isolation.

FIG. 5 is a bottom view of the base of FIG. 1 in insolation.

FIG. 6 is a top perspective view of the platform of FIG. 1 in isolation.

FIGS. 7 and 8 are a side elevation and a bottom view of the platform of FIG. 1 respectively.

FIG. 16 is a side elevation and FIG. 17 a perspective view of a staple of FIG. 11, in accordance with an embodiment.

FIG. 18 is a perspective view and FIG. 19 a side elevation of a peg, in accordance with an embodiment, providing an alternative to a staple for coupling the side mount kinematic platform of FIG. 9 to a bone.

FIGS. 22, 23 and 24 show the impactor of FIG. 21 in isolation.

FIGS. 34 and 35 are flowcharts of respective operations in accordance with respective embodiments.

DETAILED DESCRIPTION

Various relative position terms are used herein such as top, upper, under, laterally, below, etc. The relative positions reference positions of the respective objects or portions thereof when in use, for example, when coupled to a bone. In general use, the bone is coupled under the tracker mounting apparatus described herein.

Side Mount Kinematic Platform I

Figure 1:
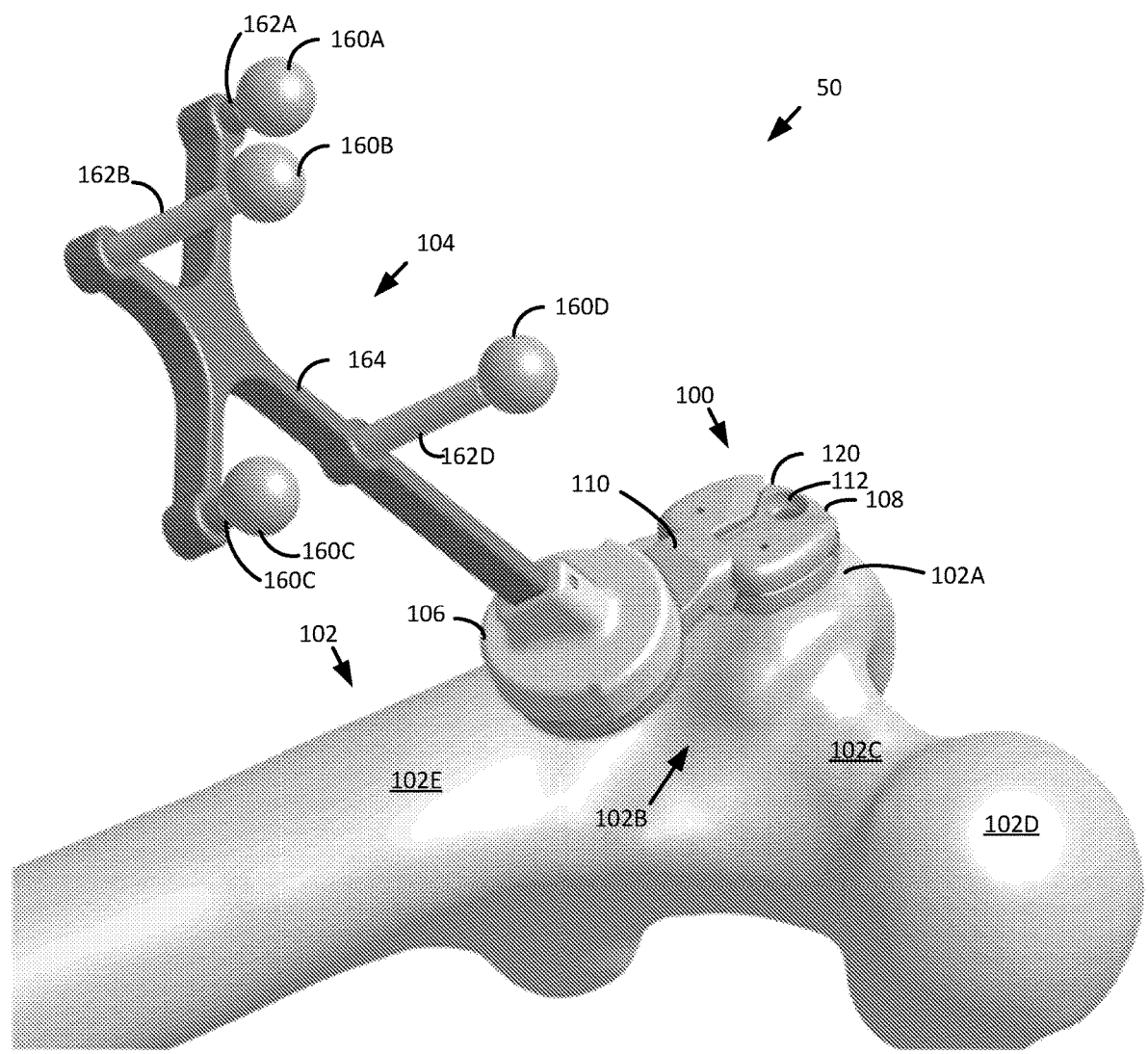
FIG. 1 is an illustration showing a perspective view of a tracker assembly comprising a side mount kinematic platform, in accordance with an embodiment, where the side mount kinematic platform is positioned for coupling to a femur and where the side mount kinematic platform is in assembly with a tracker having a quick connect mechanism.

FIG. 1 is an illustration showing a perspective view of a tracker assembly 50 comprising a side mount kinematic platform 100, in accordance with an embodiment. Side mount kinematic platform 100 is positioned for coupling to a femur 102. Side mount kinematic platform 100 is further shown in assembly with a tracker 104 having a quick connect mechanism 106 for removable connection to the side mount kinematic platform 100. Side mount kinematic platform 100 is coupled to the femur via a coupling base 108 as further described.

Figure 2:
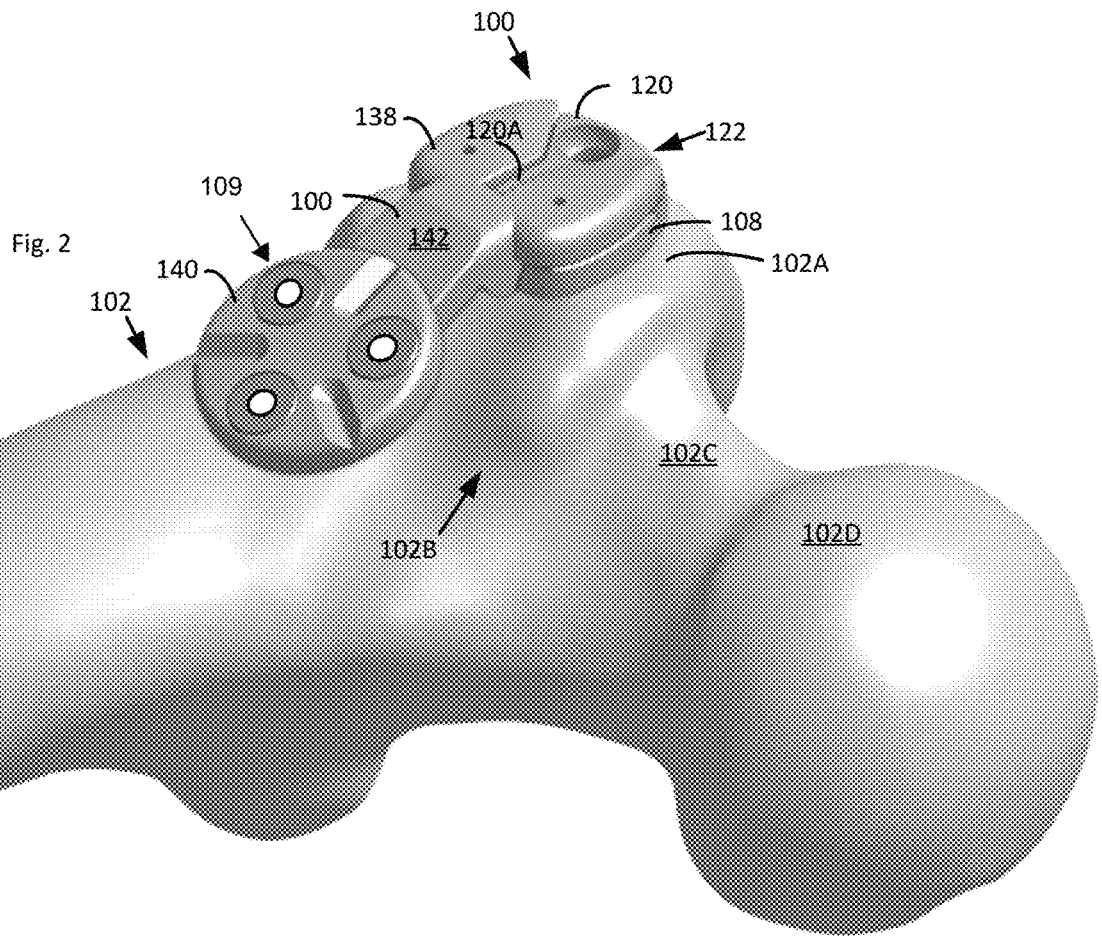
FIG. 2 illustrates the side mount kinematic platform of FIG. 1 positioned on the femur 102 but without the tracker.
Figure 3:
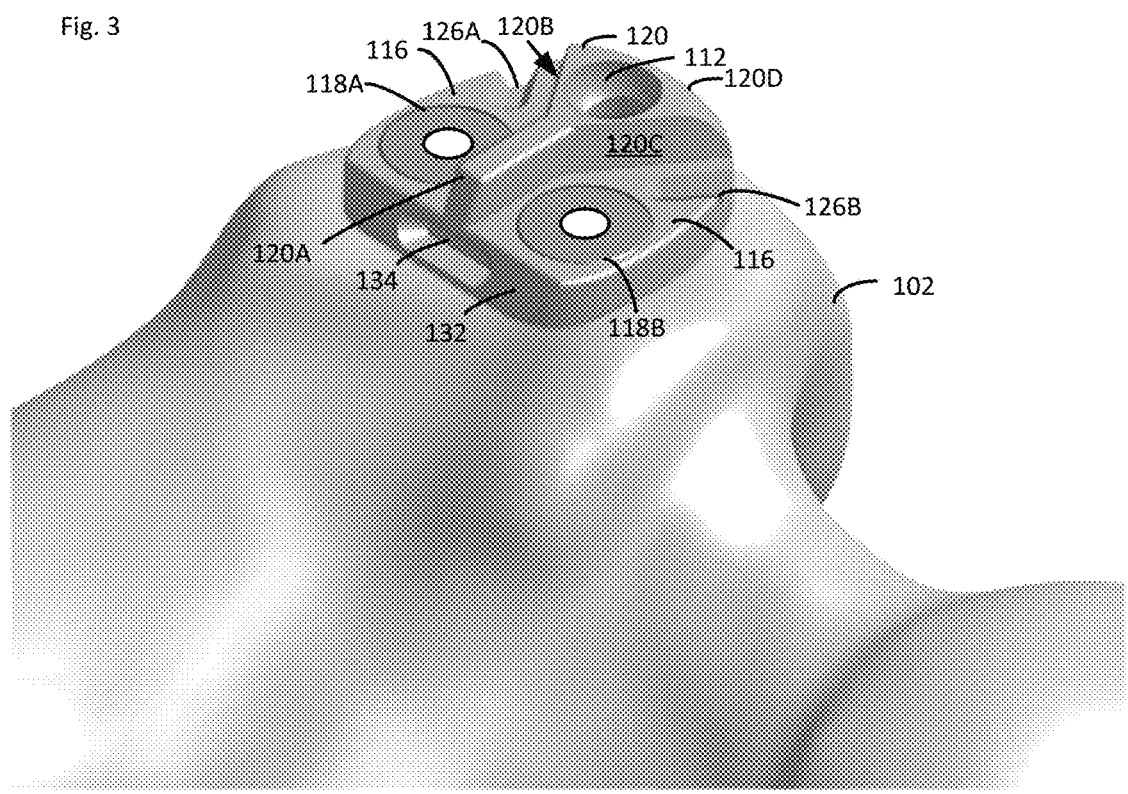
FIG. 3 illustrates only a base of the side mount kinematic platform of FIG. 1 positioned on the femur.

FIG. 2 shows coupling base 108 of FIG. 1 positioned on the femur 102 but without tracker 104. FIG. 3 shows only the coupling base 108 of FIG. 1 positioned on the femur 102.

FIG. 4 is top perspective view of coupling base 108 of FIG. 1 in isolation and FIG. 5 is a bottom view of coupling base 108 of FIG. 1 in insolation. FIG. 6 is a top perspective view of platform 100 of FIG. 1 in isolation and FIGS. 7 and 8 are a side elevation and a top view of platform 100 of FIG. 1, respectively.

Coupling base 108 defines an aperture 112 for receiving a bone screw (e.g. a fastener (not shown)) to couple the coupling base 108 to the femur 102. In an embodiment, aperture 112 is angled from normal (e.g. 10°) to direct the bone screw toward the lateral side of the femur 102 (e.g. toward a back of the coupling base 108), when in use. Coupling base 108 can be impacted into the femur 102, for example, prior to applying the fastener. Coupling base 108 provides spikes or other projections (e.g. 113A and 113B) from a bone engaging surface 114 (FIG. 5) to assist coupling base 108 to adhere to the femur 102 when impacted.

In use, in an embodiment such as shown in FIGS. 1 to 3, coupling base 108 is positioned on a first portion of the bone, which in an embodiment as illustrated is on the greater trochanter 102A and oriented such that platform 100, when mounted to coupling base 108, extends generally parallel to or away from the intertrochanteric line 102B of femur 102. That is, platform 100 is positioned remotely from neck 102C to provide access to the neck 102C and head 102D. The greater trochanter 102A provides a base engaging surface to securely receive the bone engaging surface 114 of coupling base 108. That is, the bone engaging surface 114 is relative flat and of sufficient size.

Greater trochanter 102A also provides sufficient bone material under its base engaging surface to receive the bone screw securely while lessening cracking or splitting of the bone compared to other portions of the femur in this proximal portion, particularly portions closer to or including the shaft 102E. Further, the position of the bone screw on the greater trochanter, directed toward the lateral side of the femur, avoids penetration of a portion of the bone screw into the shaft 102E, for example, without impeding access to the interior of the shaft 102E for any tool or implant. The size and shape of coupling base 108 can be configured to fit a typical area (e.g. measured in cm² or other units) presented by a typical greater trochanter. In an embodiment, the base is sized for an adult.

Coupling base 108 presents an opposing surface 116 to bone engaging surface 114. Opposing surface 116 (e.g. defining an upper surface, when in use) supports a pair of magnets 118A and 118B in respective magnet chambers in the coupling base 108 such that the magnets 118A and 118B are generally flush with the opposing surface 116. The magnets 118A and 118B couple to platform 100 as further described.

Projecting from opposing surface 116 is a platform guide 120. In an embodiment, platform guide 120 is generally "Y" shaped such that a narrow end 120A of the platform guide 120 is received in a cooperating recess 122 having a slot 122A formed in platform 100. The recess 122 cooperates in that it has a similar shape to (at least partially) receive the Y-shaped platform guide 120. Reception of the platform guide 120 in the recess 122 and its slot 122A guides the platform 100 into a mating position over the coupling base 108, as further described.

The platform guide 120 and recess 122 constrain the angle of approach of the platform 100 to mounted coupling base 108. Further, platform guide 120 assists to position the platform 100 on the coupling base 108 such that platform 100 extends in a selected direction over the femur 102. Platform guide 120 gives a visual clue to the position of the base. Narrow end 120A can be aligned with the intended direction of a longitudinal axis 124 (FIGS. 6 and 8) of the platform 100. That is, the narrow end 120A points parallel to or slightly away from the intertrochanteric line 102B and coupling base 108 can be aligned as described before mounting (e.g. impacting) the coupling base 108 to femur 102.

Opposing surface 116 forms a pair of channels 126A, 126B. The channels 126A, 126B are spaced from the surfaces 120B, 120C of the platform guide 120 (e.g. from the wide end 120D of the platform guide 120), each running respectively parallel to the surfaces 120B, 120C and each extending to a respective peripheral edge 128A, 128B of coupling base 108. The channels 126A and 126B are shaped and dimensioned for respectively receiving cooperating projections (e.g. spherical dimples) 130A and 130B of platform 100 (FIG. 8). In an embodiment, the channels 126A and 126B comprise angled trenches.

The front end of coupling base 108 has an end surface 132 in which is formed a slot 134 that is shaped and dimensioned to receive a cooperating projection 136 (e.g. dimple or tab) of platform 100 as further described.

Platform 100 comprises a unitary body 111, constructed from a single piece of material, to define a proximal member 138, a distal member 140 and an extension member 142. The proximal member is configured to couple via a base coupling interface 107 to coupling base 108, the distal member 140 is configured to couple via a tracker coupling interface 109 to tracker 104 (via the tracker's 104 quick connect mechanism 106) and the extension member 142 is configured to extend between and space apart the proximal and distal members 138 and 140. The extension member defines a lateral offset between the proximal member 138 and the distal member 140 so that the tracker 104 does not couple over the base to which the proximal member couples. That is the tracker does not couple along a central axis 400 perpendicular to the coupling base 108).

In an embodiment, extension member 142 spaces the proximal and distal members 138 and 140 in an angled relationship "θ" (FIG. 7) so that, when in position on the bone, an under surface 144 of the extension member 142 and an under surface 146 of the distal member 140 follows generally a contour of the adjacent surface of the bone, for example the contour of the femur 102 extending from the greater trochanter. Further, in the illustrated embodiment, the extension member is angled such that a plane occupied by an upper surface of the proximal member is different from a plane occupied by the upper surface of the distal member. As well, under surface 146 does not contact the bone surface.

An under surface 148 of proximal member 138 is configured to mate with opposing surface 116 of coupling base 108. Under surface 148 presents magnets 150A and 150B positioned for mating engagement with magnets 118A and 118B. Under surface 148 further presents the projections 130A and 130B for engagement with channels 126A and 126B. Extension member 142 comprises a first end 152 that supports the projection 136 for mating with slot 134. It is understood that the projections could be configured on the base and the respective slot and channels could be configured on the arm. The projections may be better suited to the platform 100 as the base can be subject to impacting.

Two magnets are provided on each of the base and platform interfaces. The magnets are slightly offset so that the platform is pulled into the base when positioned to draw closer to the base. That is, magnets 118A and 118B are slightly farther from edge 132 (than are magnets 150A and 150B of the cooperating interface) so that when magnets 150A and 150B are in close proximity to magnets 118A and 118B, there is a magnetic force directing recess 122 toward and adjacent to platform guide 120 as well pulling the two mating surfaces (148 to 116) together. The spherical dimples provide a constrained mechanical connection to the base while the base accepts the dimples in angled trenches. When finally mated such that when projections 130A, 130B, and 136 are seated in their respective channels 126A, 126B and slot 134, the Y-shaped platform guide 120 does not contact a surface of recess 122 (i.e. it is spaced slightly therefrom).

The magnet and projection features of the platform 100 at proximal member 138 and extension member 142, and the magnet, channel and slot features of the coupling base 108 contribute to provide a repeatable, quick connect mechanism so that the platform 100 can be coupled to the coupling base 108. The relative mating position is consistent (along constrained degrees of freedom) and is sufficiently secure. The attractive force is sufficient to support the coupling of the platform and base and the tracker and platform under respective weights. A user need not hold the assembly to maintain it in the assembled position when in use.

An upper surface 153 of distal member 140 is configured with the tracker coupling interface 109 to cooperatively mate with an under surface (not shown) of quick connect mechanism 106, in accordance with an embodiment. As shown, upper surface 153 is configured to provide three radially spaced magnets 154A, 154B and 154C and three radially spaced channels 156A, 156B and 156C respectively interposed between the magnets 154A, 154B and 154C. An under surface of the quick connect mechanism 106 presents three radially spaced magnets (not shown) and radially space projections (not shown) similarly interposed between the mechanism's magnets so that when the mechanism 106 and distal member are positioned toward one another, the respective under surface and upper surface 153 engage in a mating relationship. The projections align the tracker and the attractive force of the magnets is utilized to draw the components together. Moreover, the relative mating position is consistent (along constrained degrees of freedom) and sufficiently secure. The magnetic attraction is sufficient to secure the tracker to the distal member without movement (e.g. the weight of the tracker is supported when coupled). A user need not hold the assembly to maintain it in the assembled position when in use.

The coupling between the platform 100 and coupling base 108 is constrained in 6 degrees of freedom. That is, below a threshold amount of force to disengage the coupling (e.g. to overcome the magnetic attraction or any friction coupling), the platform is fixed to the base and does not move in any direction.

The primary components (e.g. excluding magnets) of the coupling base 108 and platform 100 may be constructed of medical grade materials including titanium, aluminum, or non-ferrous stainless steel as examples. The components may be constructed by forging, casting, or subtractive manufacturing methods, etc. as is well known.

The quick connect mechanism 106 and upper surface 153 of distal member 140 enable the tracker to be quickly coupled and if desired, later removed and recoupled in a repeatable manner during a procedure without disturbing a registration of components within a coordinate system of a localization system (not shown). The base remains coupled (i.e. in a fixed position) to the bone. The platform can be removed and replaced in a highly repeatable position. In some workflows, tracker can be removed for coupling to other objects including another portion of patient anatomy before returning to couple to upper surface 153. Quick connect mechanism 106 is useful to couple the tracker to such other objects.

Examples of quick connect mechanisms are described in U.S. 9,247,998B2, published Feb. 2, 2016, which is incorporated herein by reference in its entirety. Quick connect mechanism 106 and surface 153 may take other forms such as described therein.

Tracker 104 represents a conventional tracker to provide tracking information to a localization system (e.g. via an optical sensor of the localization system). Tracker 104 comprises an array of passive light sources 160A, 160B, 160C and 160C on respective posts 162A, 162B, 162C and 162C coupled to a generally "t" shaped support body 164. Generally spherical reflective light sources are shown. Typical reflective light sources provide good reflective properties in the infrared spectrum. It is known that active light sources, light sources having different shapes, and a different quantity of light sources can each be used in alternative constructions. Examples of trackers are further described in U.S. 9,247,998B2, published Feb. 2, 2016, which is incorporated herein by reference in its entirety.

Hence, side mount kinematic platform 100 provides a mount offset via extension member. Instead of attaching the tracker 104 directly over a base platform mounted to the bone, a side mount offset is enabled so that the device to bone fixation location does not need to be directly visible in the incision at the time of measurement. The attachment area can be exposed using surgical retractors to move soft tissue or internally rotating the femur to gain access to the lateral greater trochanter. An embodiment of a method of use is described further herein with reference to FIG. 33.

A registration can be performed with the tracker assembly 50 positioned on the bone as described. The tracker can be removed and replaced and at least one of guidance and a measurement can be generated and presented from a localization system without undergoing a second (subsequent) registration. The localization system can provide measurements and guidance using the same single registration for initial or subsequent placements of the tracker on the platform in a same position that was used for the same single registration. In an embodiment, the localization system tracking the tracker and providing measurements need not be configured with any offset information. A pose of the tracker when assembled as assembly 50, is recorded by the localization system and this is recorded as the femur orientation. At subsequent measurements, deltas are computed based on the initial measurement.

Side Mount Platform II—Pivoting Platform

Figure 9:
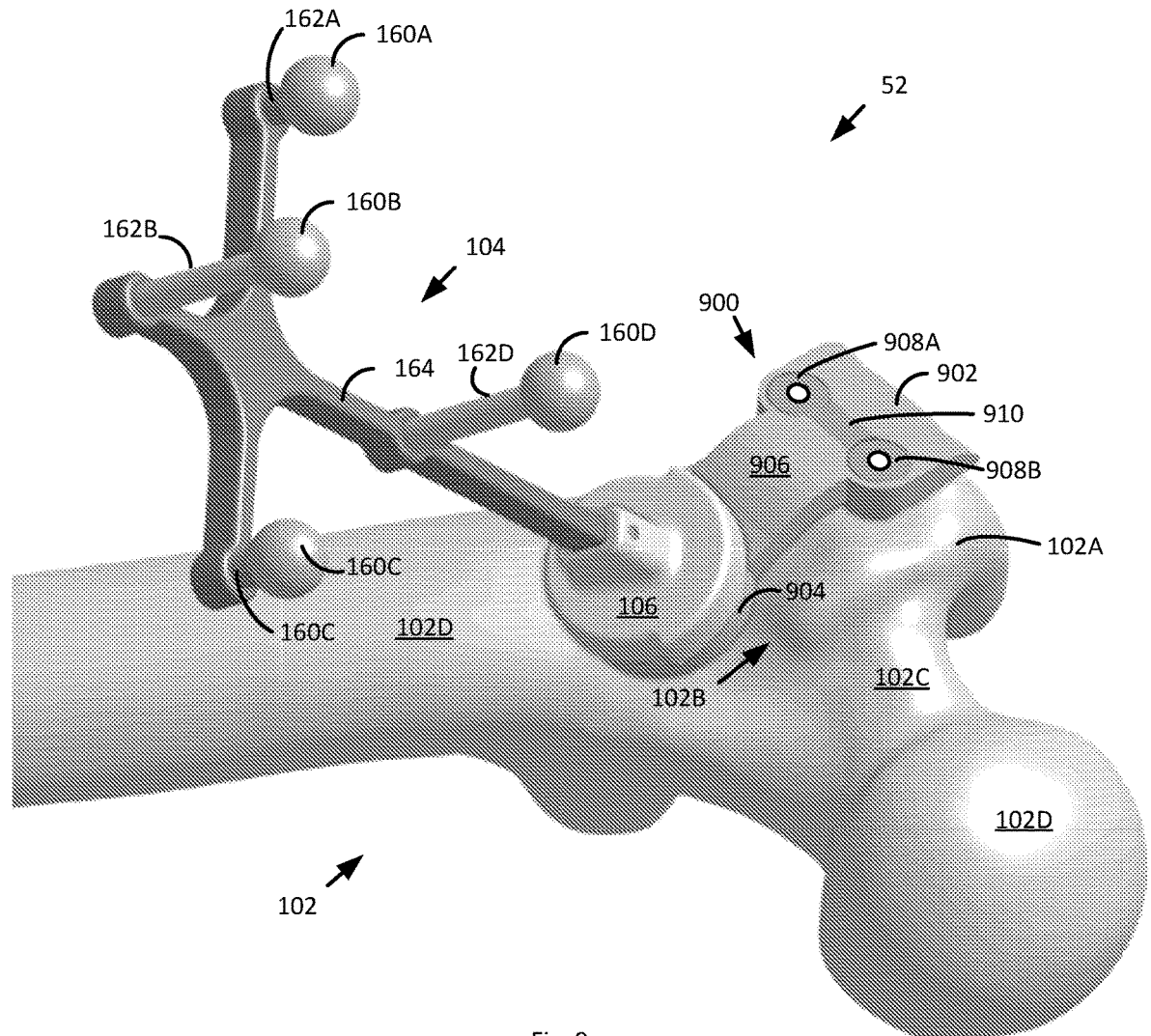
FIG. 9 is an illustration showing a perspective view of a tracker assembly comprising a side mount kinematic platform, in accordance with an embodiment, where the side mount kinematic platform is coupled to a bone (e.g. a femur) and where the side mount kinematic platform is in assembly with a tracker having a quick connect mechanism.
Figure 10:
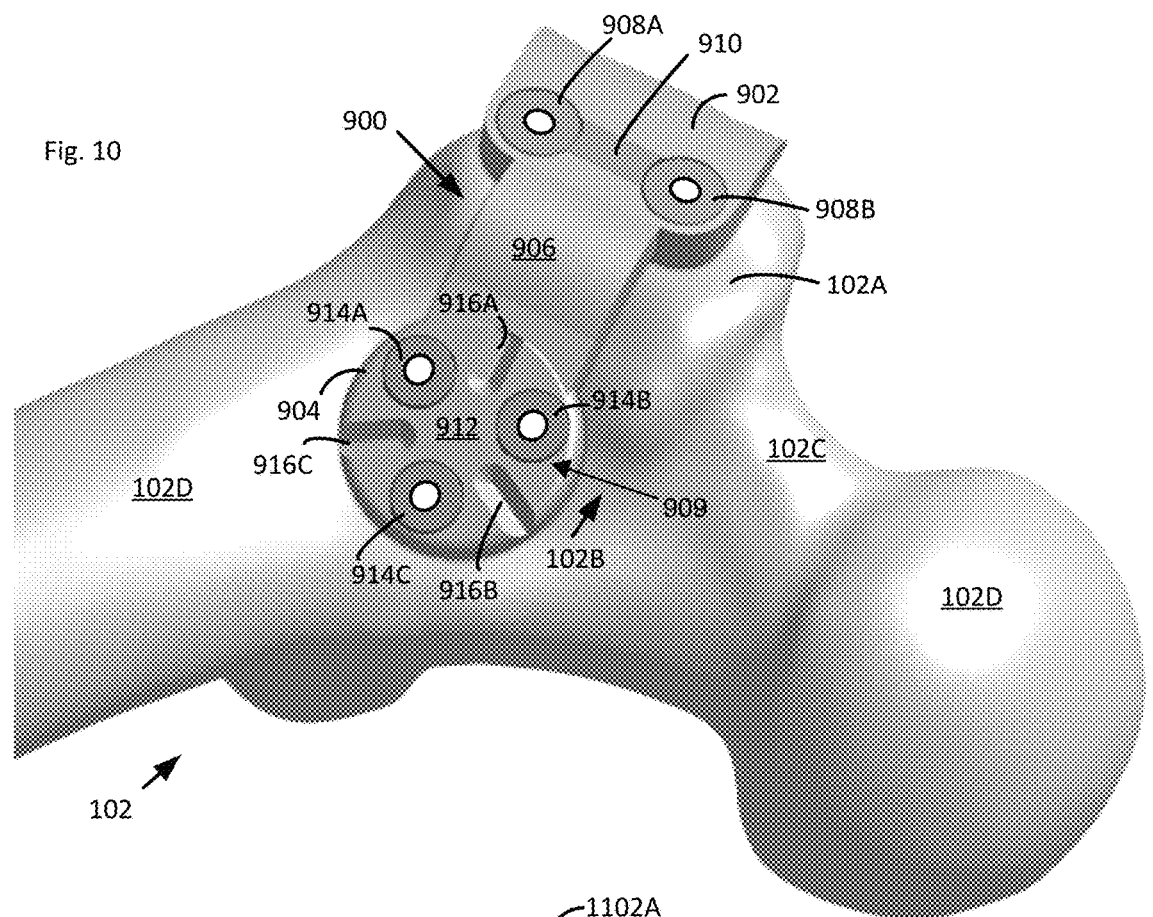
FIG. 10 illustrates the side mount kinematic platform of FIG. 9 positioned on the bone but without the tracker.
Figure 11:
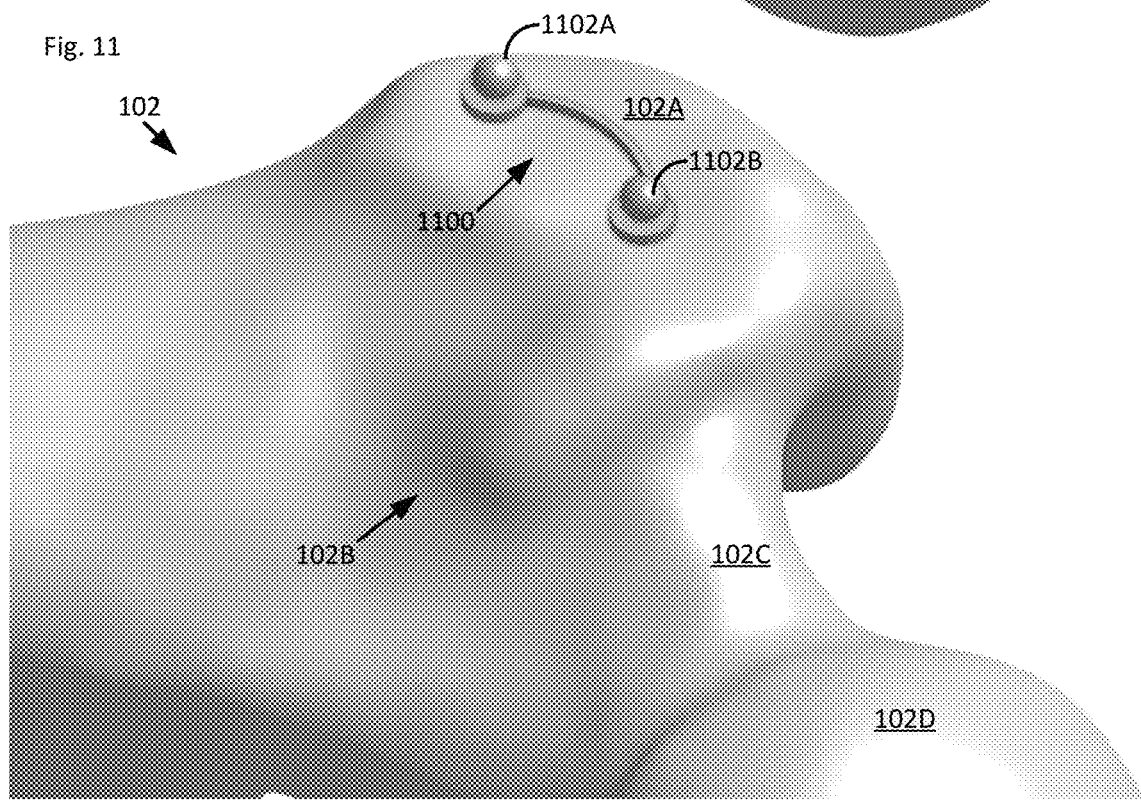
FIG. 11 illustrates a staple, in accordance with an embodiment, positioned on the bone for coupling the side mount kinematic platform of FIG. 9 to the bone.

FIG. 9 is an illustration showing a perspective view of a tracker assembly 52 comprising a side mount kinematic platform 900, in accordance with an embodiment, where the side mount kinematic platform 900 is coupled to a femur 102 and where the side mount kinematic platform 900 is in assembly with a tracker 104 having a quick connect mechanism 106. FIG. 10 illustrates the side mount kinematic platform 900 of FIG. 9 positioned on the femur 102 but without the tracker 104. FIG. 11 illustrates only a coupling base, in accordance with an embodiment, comprising a staple 1100 positioned on the femur 102 for coupling the side mount kinematic platform 900 of FIG. 9.

Figure 12:
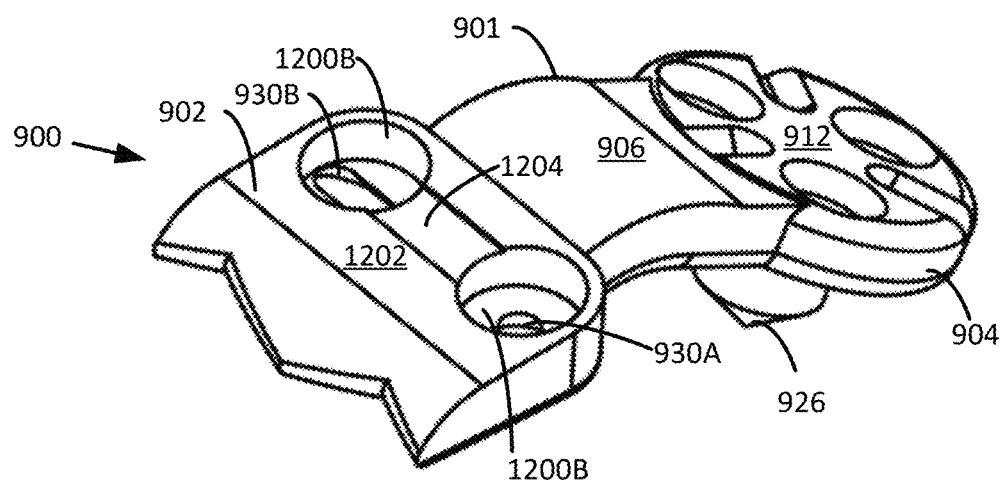
FIG. 12 is top rear perspective view of the side mount kinematic platform of FIG. 9 in isolation and without magnets.
Figure 13:
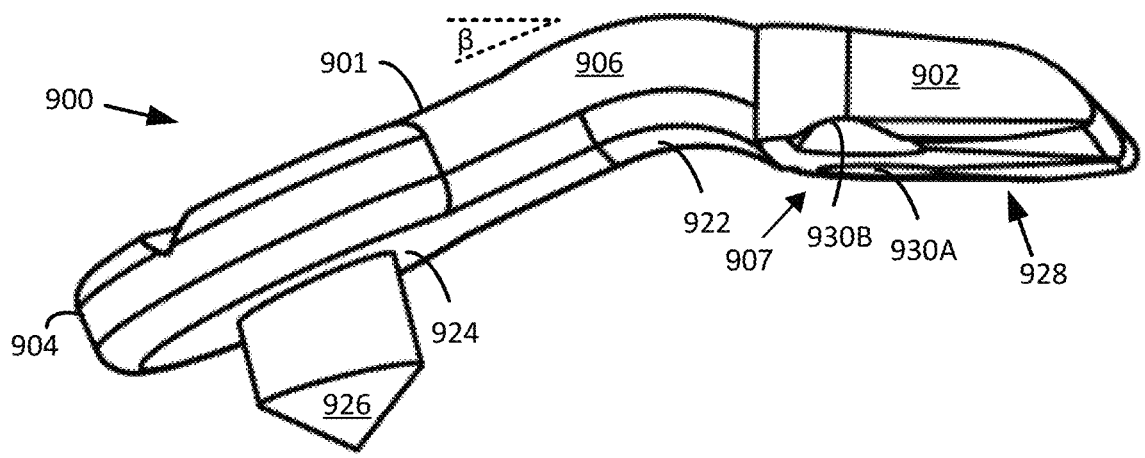
FIG. 13 is a side bottom perspective view of the side mount kinematic platform of FIG. 9 in insolation and without magnets.
Figures 14, 15:
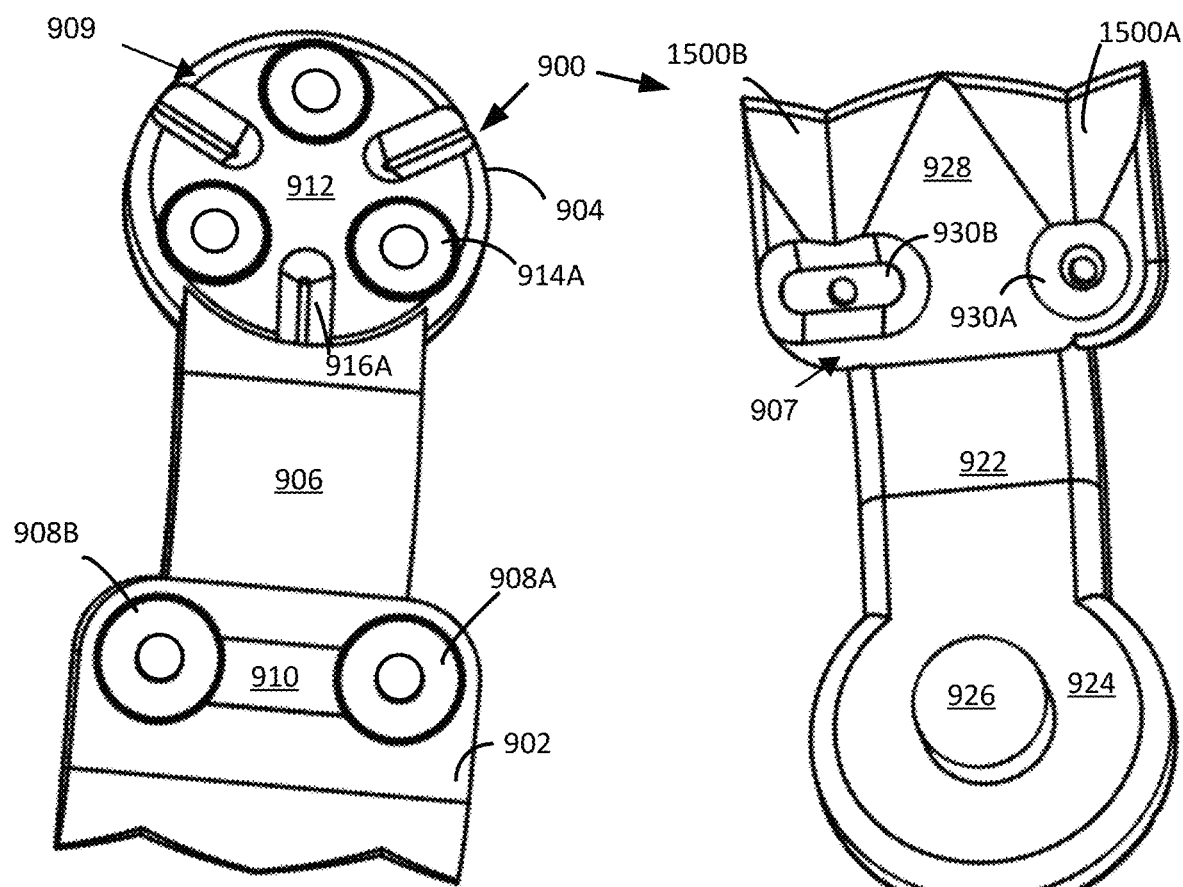
FIG. 14 is a top perspective view from a proximal end of the side mount kinematic platform of FIG. 9 in isolation.
FIG. 15 is a bottom perspective view from a distal end of the side mount kinematic platform of FIG. 9 in isolation.

FIG. 12 is top rear perspective view of the side mount kinematic platform 900 of FIG. 9 in isolation and without magnets. FIG. 13 is a side bottom perspective view of the side mount kinematic platform 900 of FIG. 9 in insolation and without magnets. FIG. 14 is a top perspective view from a proximal end of the side mount kinematic platform 900 of FIG. 9 in isolation. FIG. 15 is a bottom perspective view from a distal end of the side mount kinematic platform 900 of FIG. 9 in isolation.

Similar to side mount kinematic platform 100, side mount kinematic platform 900 provides an offset for mounting tracker 104. Side mount kinematic platform 900 comprises a unitary body 901, constructed from a single piece of material, to define a proximal member 902, a distal member 904 and an extension member 906. The proximal member 902 is configured to carry a pair of magnets 908A and 908B connected via a ferrous bridge body 910 (providing a ferrous coupler) to couple the proximal member 902 to a bone, for example femur 102, via a coupling base as further described. In an embodiment, the coupling comprises a pivoting coupling as further described.

Distal member 904 is configured to couple via a tracker coupling interface 909 to tracker 104 (via the tracker's 104 quick connect mechanism 106) and the extension member 906 is configured to extend between and space apart the proximal and distal members 902 and 904 to contribute to a lateral offset feature. The extension member spaces the ends of the body to space the tracker coupling interface from the bone coupling interface. With reference to the respective anatomy and the tracker assembly in an embodiment as illustrated, the extension member moves the connection point of the connect mechanism 106 medially and distally from the bone attachment interface (e.g. coupling base) on the lateral greater trochanter.

Similar to platform 100, an upper surface 912 of distal member 904 is configured to provide a cooperative interface to mate with an under surface (not shown) of quick connect mechanism 106, in accordance with an embodiment. As shown, upper surface 912 presents three radially spaced magnets 914A, 914B and 914C and three radially spaced channels 916A, 916B and 916C respectively interposed between the magnets 914A, 914B and 914C. The under surface of the quick connect mechanism 106 presents three radially spaced magnets (not shown) and radially spaced projections (not shown) similarly interposed between the mechanism's magnets so that when the mechanism 106 and distal member are positioned toward one another, the respective under surface and upper surface 912 engage in a mating relationship. The projections align the tracker and the attractive force of the magnets is utilized to draw the components together. Moreover, the relative mating position is consistent (along constrained degrees of freedom) and sufficiently secure. The magnetic attraction is sufficient to secure the tracker to the distal member without movement (e.g. the weight of the tracker is supported when coupled). A user need not hold the assembly to maintain it in the assembled position when in use. Similar to the interface between the platform 100 and the tracker 104, the quick connect mechanism 106 and upper surface 912 of distal member 904 enable the tracker 104 to be quickly coupled and if desired, later removed and recoupled in a repeatable manner during a procedure without disturbing a registration of components within a coordinate system of a localization system (not shown).

Extension member 906 spaces the proximal and distal members 902 and 904 to provide a lateral offset so that the tracker coupling interface of the distal platform is laterally spaced from the position at which the proximal member is coupled to the bone. Similar to assembly with platform 100, the tracker does not couple over the proximal member (e.g. not along a central axis perpendicular to the proximal member).

In an embodiment, extension member 906 also spaces the proximal and distal members 902 and 904 in an angled relationship "β" (FIG. 13). When in position on the bone (e.g. 102), an under surface 922 of the extension member 906 and an under surface 924 of the distal member 904 follows generally a contour of the adjacent surface of the bone, for example, the contour of the femur extending from the greater trochanter. The under surface 922, in the embodiment, does not rest upon or contact the surface of the bone when installed. Further, the extension member is angled such that a plane occupied by an upper surface of the proximal member is different from a plane occupied by the upper surface of the distal member.

In an embodiment, under surface 924 of the distal member 904 provides a bone engaging projection 926 in the form of a conical bone engaging projection 926 (e.g. FIGS. 12, 13 and 15) with which to engage a portion of the bone surface. The conical bone engaging projection 926 is further described with reference to the coupling of the proximal member 902 via the coupling base.

FIG. 16 is a side elevation and FIG. 17 a perspective view of the staple 1100 defining the couple base according to an embodiment. FIG. 18 is a perspective view and FIG. 17 a side elevation of a portion of an alternative coupling base comprising a peg 1800, in accordance with an embodiment. When employed in a pair of pegs (e.g. 1800) as further described, the pair provides an alternative to staple 1100 for coupling the side mount kinematic platform of FIG. 9 to the bone.

The coupling of the proximal member to the bone, in respective embodiments, is obtained using a coupling base comprising a single staple 1100 or a pair of pegs (e.g. each 1800). An under surface 928 of proximal member 902 is configured (via a base coupling interface 907) to mate with spaced spherical tips (e.g. spherical projections 1102A and 1102B or a pair of 1802). The under surface 928 forms one or more recesses (e.g. 930A and 930B) to receive the respective tips. If more than one recess (e.g. 930A, 930B) is provided, the recesses are spaced, for example, to match the spacing of the spherical projections 1102A and 1102B in staple 1100 or the intended spacing of a pair of pegs when impacted into the bone. It can be challenging to impact pegs at a predetermined distance. In an embodiment, one recess e.g. 930A is generally circular at its opening to define a socket to receive a tip in a constrained manner. The use of a socket constrains movement of the platform 900 in a number of degrees of freedom. The other recess e.g. 930B in the present embodiment defines a channel such as an angled trench. A channel is useful to receive a tip that is spaced at distance from another tip within a threshold of tolerance from the tip received in recess 930A defining the socket. This variation in distance may arise by manufacturing tolerances related to the construction of the staple or through impact when implanting the staple or pegs. In another embodiment, not shown, two sockets are provided, which may require very accurate tip spacing. A method of coupling a pivoting side mounted platform and coupling base and an impactor tool are described later herein.

As shown in FIGS. 15-18, the staple 1100 and peg 1800 can comprise barbs (e.g. 1104A, 1104B) or rings (1804) on respective shafts 1106A, 1106B, 1806 to grip bone material to secure the coupling base. It is understood that staples can have rings and pegs can have barbs.

In an embodiment, the recesses 930A, 930B are positioned under the magnets 908A and 908B and can be at least partially under ferrous bridge body 910 providing a ferrous coupler. FIG. 12 shows the unitary body 901 of platform 900 without any magnets. The recesses 930A, 930B are visible through magnet chambers 1200A and 1200B formed in the upper surface 1202 of proximal member 902. Also shown is a bed 1204 formed in the surface 1202 to receive ferrous bridge body 910. The magnets 908A and 908B inserted in the proximal member 902 can be of opposite polarity so that when joined by a ferrous bridge the magnetic pull is increased on the spheres of the staple. This has the effect of completing a magnetic loop using the dipoles created by using opposite polarity magnets. This additional strength is lost if two independent sphere pegs are used instead of the staple.

The magnets 908A and 908B provide tactile feedback when approaching and securing to the staple or peg spheres to the proximal member.

With reference to FIG. 15, surface 928 defines respective wide angled trenches that are wide at the peripheral edge and become more narrow toward the recesses 930, 930B to help guide the user to place the proximate member onto the tips of the coupling base.

The generally spherical shape of the spherical projections (e.g. 1102A, 1102B and 1802) and the cooperating shape of the recesses permits at least partial rotation of the side mount kinematic platform 900 about the axis 1103 of the coupling base. Bone engaging projection 926 constrains rotation of distal member 904 toward the bone. In other words, relative to movement analysis using classical 6 degrees of freedom, two points of contact are provided by the channel/tip interface and three more are provided by the shallow socket/tip interface. The remaining degree of freedom is rotation along the axis 1103 of the staple (a similar axis exists between the pair of pegs).

Relative to the coupling between the platform 900 and coupling base, the platform 900 is constrained in 5 degrees of freedom. That is, below a threshold amount of force to disengage the coupling (e.g. to overcome the magnetic attraction or any friction coupling), the platform is fixed to the coupling base and moves in only one direction, namely rotation about the axis as described.

When a tracker 104 is mounted to the platform on the circular interface provided by distal member 904, the weight of the tracker 104 pulls the conical contact point of projection 928 to the femur surface to constrain the last degree of freedom. A practitioner such as a surgeon can push the conical contact into the surface of the femur with sufficient force to reach bone, but not too hard as to create a bone divot. The position is repeatable if pressure is removed and reapplied. The dimension of the cone is relatively wide, increasing surface area to spread out any force applied, to prevent the sharp point of the cone from protruding deep into the bone or soft tissue, assisting to make the position more repeatable A registration can be performed with the tracker assembly 52 positioned on the bone as described. The tracker can be removed and replaced without undergoing a second registration. The localization system can provide measurements and guidance using the same single registration for initial or subsequent placements of the tracker on the platform in a same position that was used for the same single registration. In an embodiment, the localization system tracking the tracker 104 and providing measurements need not be configured with any offset information. A pose of the tracker 104, when assembled as assembly 52, is recorded by the localization system and this is recorded as the femur (bone) orientation. At subsequent measurements, deltas are computed based on the initial measurement.

Similar to platform 100, unitary body 901 can be constructed of medical grade materials as described and the ferrous bridge, which must be ferrous, can be stainless steel, as an example. The components may be constructed by the manners as described. A staple or a peg can be constructed of medical grade materials which are ferrous (e.g. stainless steel) to interact with the magnets of platform 900. The components may be constructed by stamping, cutting, casting, etc. as is well known.

Methods of Coupling a Side Mounted Platform

In accordance with one or more embodiment, there are provided methods, techniques and a tool for coupling a side mounted platform. Such methods and techniques can apply to a standard direct anterior approach for total hip arthroplasty.

Exposing a first bone surface of a bone for coupling the coupling base: In an embodiment, the femur is exposed, such as via an incision, as per the standard approach for the THA. In a THA embodiment, the bone is a femur and the first bone surface is a portion of the greater trochanter, for example, the anterior lateral surface of the greater trochanter.

Often the incision for a THA is minimally executed. To obtain access to the first bone surface, surgical retractors are used to separate soft tissues and/or an internal rotation of the bone (e.g. femur) is performed to expose the first bone surface (e.g. the anterior lateral surface of the greater trochanter).

An area of relatively flat topography and low amounts of soft tissue are preferred for coupling the applicable coupling base. In a THA embodiment, relatively flat topography and low amounts of soft tissue can be located the near the base of the femoral neck, on the greater trochanter lateral to the intertrochanteric ridge and the vastus lateralis insertion point.

Coupling a staple 1100 for a (pivoting) platform 900: In an embodiment, platform 900 and staple 1100 are selected for coupling to the bone 102 (e.g. at a first portion). An impactor tool is useful to impact the staple 1100 into the bone 102.

Figure 20:
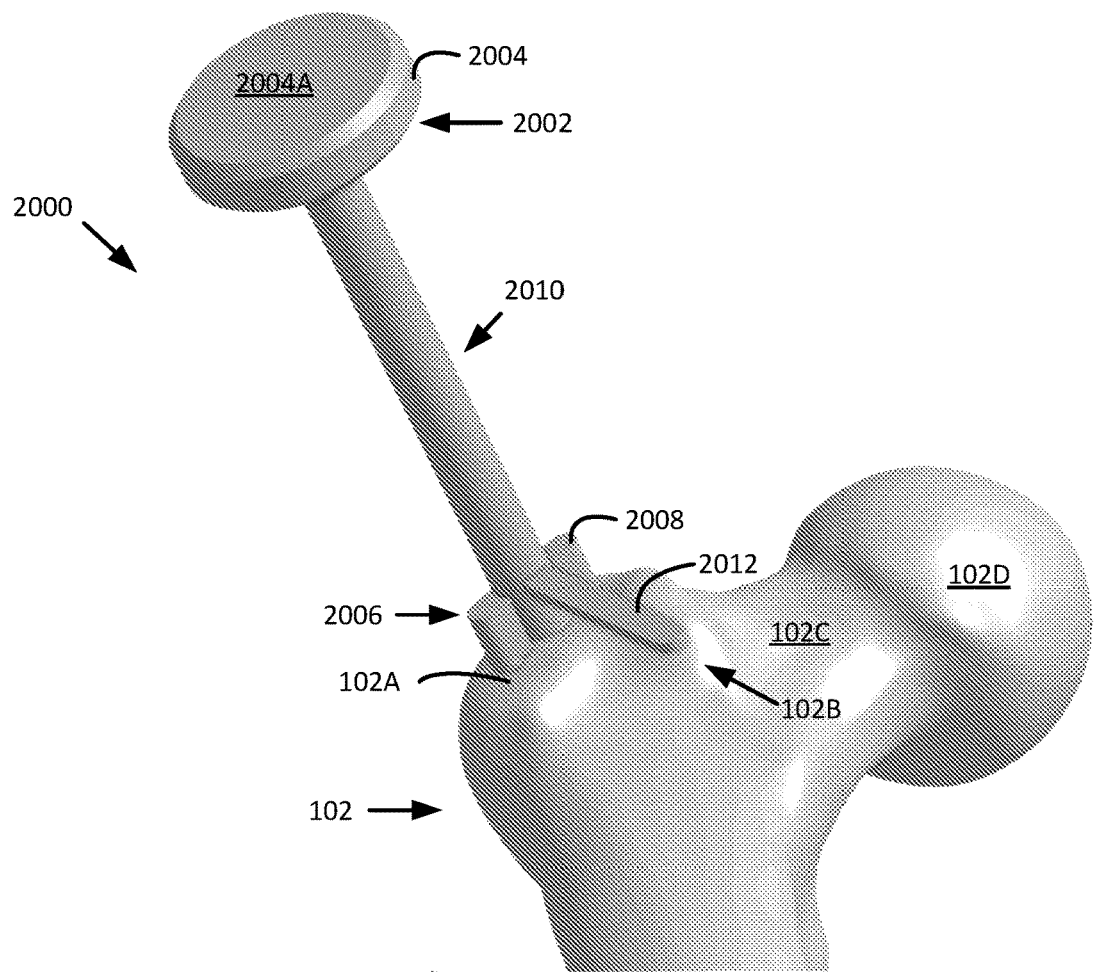
FIG. 20 illustrates a coupling base impactor mounted to femur in accordance with an embodiment.

With reference to FIG. 20, there is disclosed a coupling base impactor 2000 mounted to femur 102 at the greater trochanter 102A, lateral to the intertrochanteric ridge 102B. Coupling base impactor 2000 comprises a head end 2002 (e.g. a first end) defining an impact head 2004, a base engaging end 2006 (e.g. a second end) comprising a coupling interface 2008 for coupling to a coupling base (e.g. shaft 1100) and a shaft 2010 extending between the free end 2002 and base engaging end 2006. Impact head 2004 has an impact surface 2004A. Impactor 2000 further comprises a protruding alignment guide 2012 (e.g. in the form of a flat, straight arm) extending from shaft 2010 as further described. A length of the guide 2012 can be dimensioned to match a distance of the bone engaging projection 926 from the coupling base.

Figure 21:
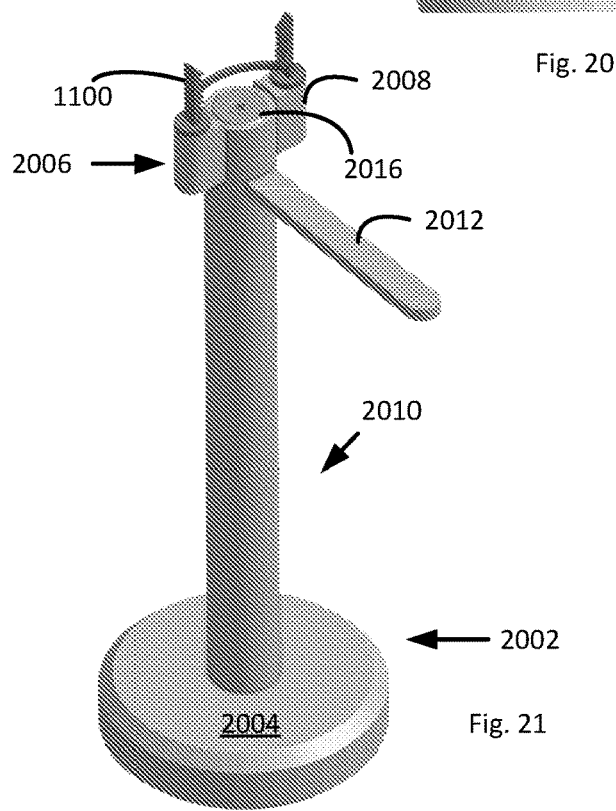
FIG. 21 shows the coupling base impactor in an inverted perspective view, relative to FIG. 20, to visualize a coupling interface.

FIG. 21 shows the coupling base impactor 2000 in an inverted perspective view, relative to FIG. 20, to visualize coupling interface 2008 that is coupled to the coupling base (staple 1100). FIGS. 22, 23 and 24 show impactor 2000 in isolation. Coupling interface 2008, in an embodiment, comprises a pair of spaced recesses 2014A and 2014B defined by base engaging end 2006 and a magnet 2016. Magnet 2016 is disposed between recesses 2014A and 2014B (e.g. in an end of shaft 2010 in a magnet chamber such that a surface thereof is exposed. Magnet 2016 may be secured to the impactor 2000 such as by a fastener or adhesive, etc. Recesses 2014A and 2014B are shaped to receive spherical projections (e.g. 1102A and 1102B of staple 1100).

Magnet 2016 provides an attractive force to couple to the ferrous material of staple 1100.

With reference to FIG. 20, there is disclosed a coupling base impactor 2000 mounted to femur 102 at the greater trochanter 102A, lateral to the intertrochanteric ridge 102B. Coupling base impactor 2000 comprises a head end 2002 (e.g. a first end) defining an impact head 2004, a base engaging end 2006 (e.g. a second end) comprising a coupling interface 2008 for coupling to a coupling base (e.g. shaft 1100) and a shaft 2010 extending between the free end 2002 and base engaging end 2006. Impact head 2004 has an impact surface 2004A. Impactor 2000 further comprises a protruding alignment guide 2012 (e.g. in the form of a flat, straight arm) extending from shaft 2010 as further described. A length of the guide 2012 can be dimensioned to match a distance of the bone engaging projection 926 from the coupling base.

For coupling a platform 900 to the bone 102, staple 1100 is placed into the impactor 2000 such that the round surfaces of spherical projections 1102A and 1102B fit inside the recessed areas 2014A and 2014B. The sharp points of 1106A and 1106B are placed near the first portion of the bone 102 (e.g. a surface at 102A). The protruding impact guide 2012 is aligned such that the staple (or individual pegs 1800 if such are used instead of the staple 1100) is in the position described herein above while the guide remains distal and approximately parallel with the intertrochanteric ridge 102B.

The distal and medial end of the impact guide 2012 indicate (e.g. at least approximately) where the point of bone engaging projection 926 of platform 900 will contact a second portion of the bone 102 when the platform 900 is coupled to the staple 1100 on the bone 102.

Once in place, touch the sharp points 1106A and 1106B to the first surface 102A Impactor head 2004 is impacted at surface 2004A to drive the staple 1100 in the direction along the linear shaft 2010 of the impactor 2000 into the bone surface at 102A until the staple 1100 is seated in the bone 102.

Coupling a Base 108 for Side Mount Kinematic Platform 100:

Base 108 is positioned on the bone surface of the greater trochanter 102A such that the screw hole 112 is proximal and lateral. The narrow end of the Y-shaped protrusion 120A is located medial and distal to screw hole 112 such that the narrow end 120A is approximately parallel to the intertrochanteric ridge 102B.

Using any applicable surgical impacting tool, a top surface of base 108 is impacted down along the normal 400 so that spikes 113A and 113B engage the bone surface.

A spherical head screw of 18 mm or similar as applicable (not shown) is placed into aperture 112 and tightened to fix the base 108 to the bone surface.

Coupling a Side Mount Platform to Its Coupling Base:

With a respective coupling base coupled to the bone 102, surgical retractors (not shown) are released (e.g. at least partially released) as can be necessary to move the bone 102 to the desired measurement position. The bone 102 can be rotated as needed to move the patient anatomy (e.g. a leg) into a desired position for measurement such as an anatomical neutral position.

Tracker 104 is connected to the side mount kinematic platform 100 or 900 using interface 106 and the applicable tracker coupling interface 109 or 909 of the platform 100 or 900.

Side mount kinematic platform 100 or 900 is positioned onto its applicable coupling base (e.g. 108 for platform 100, or 1100/1800 for platform 900) using the base coupling interface 107 or 907 of the first end of the respective platform. The respective platform 100 or 900 is positioned by bring the respective surfaces of the platform to the mating surfaces of the respective coupling bases together until the magnetic attraction force links and constrains the two devices. It will be appreciated that side mount kinematic platform 100 or 900 can be coupled to the applicable coupling base and then the side mount kinematic platform 100 or 900 and tacker 104 can be coupled together.

For the pivoting platform 900, the platform 900 is rotated about the staple axis 1103 until the sharp point of bone engaging projection 926 contacts the bone surface (e.g. at the second portion of the bone).

Respectively, tracker assemblies 50 and 52 are in place, ready to register the orientation of the tracker 104.

Figure 25:
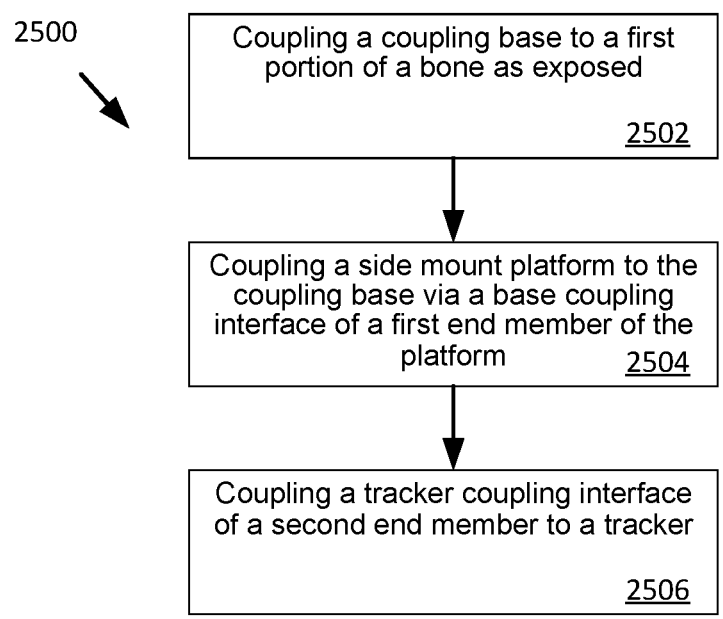
FIG. 25 is a flowchart of operations in accordance with an embodiment.

FIG. 25 is a flowchart of operations 2500 in accordance with an embodiment. At step 2502, a coupling base is coupled to a first portion of a bone as exposed. AT step 2504, a side mount platform is coupled to the coupling base via a base coupling interface of a first end member of the platform, the platform comprising body having the first end member and a second end member laterally connected to and spaced from the first end by an extension member of the body. At 2506, a tracker coupling interface of the second end member is coupled to a tracker.

In an embodiment, prior to coupling the coupling base to the first portion of the bone: an incision is performed through soft tissue adjacent to the first portion of the bone; the soft tissue are retracted to expose the first portion for coupling the coupling base; and the soft tissue are at least partially released, wherein when coupled, the first end member is positioned away from the incision. That is the first end member can be positioned under soft tissues that have relaxed from resection back toward the line of incision.

Neck Resection Guided Platform

Figure 26:
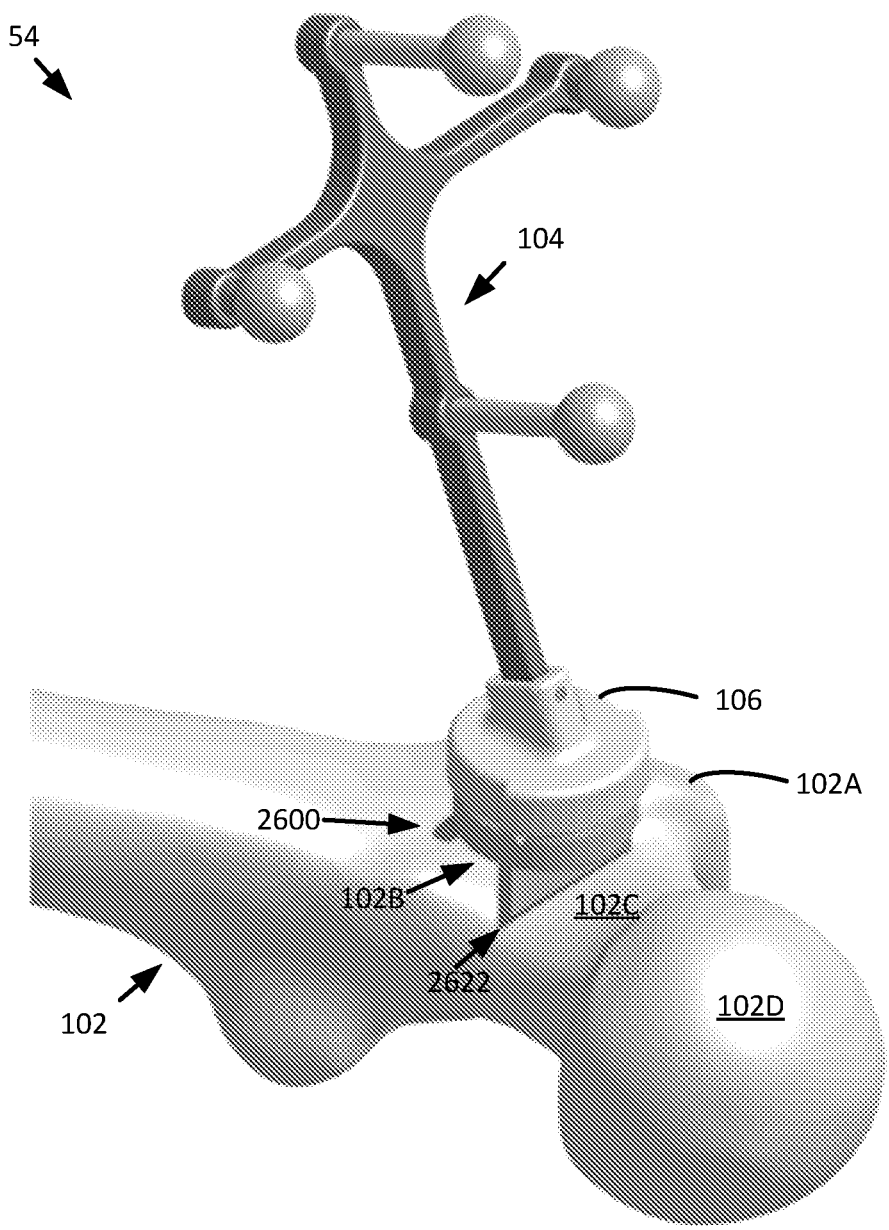
FIG. 26 is an illustration showing a perspective view of a tracker assembly comprising a neck resection guided platform, in accordance with an embodiment, where the platform is coupled to a femur and where the platform is in assembly with a tracker having a quick connect mechanism.
Figure 27:
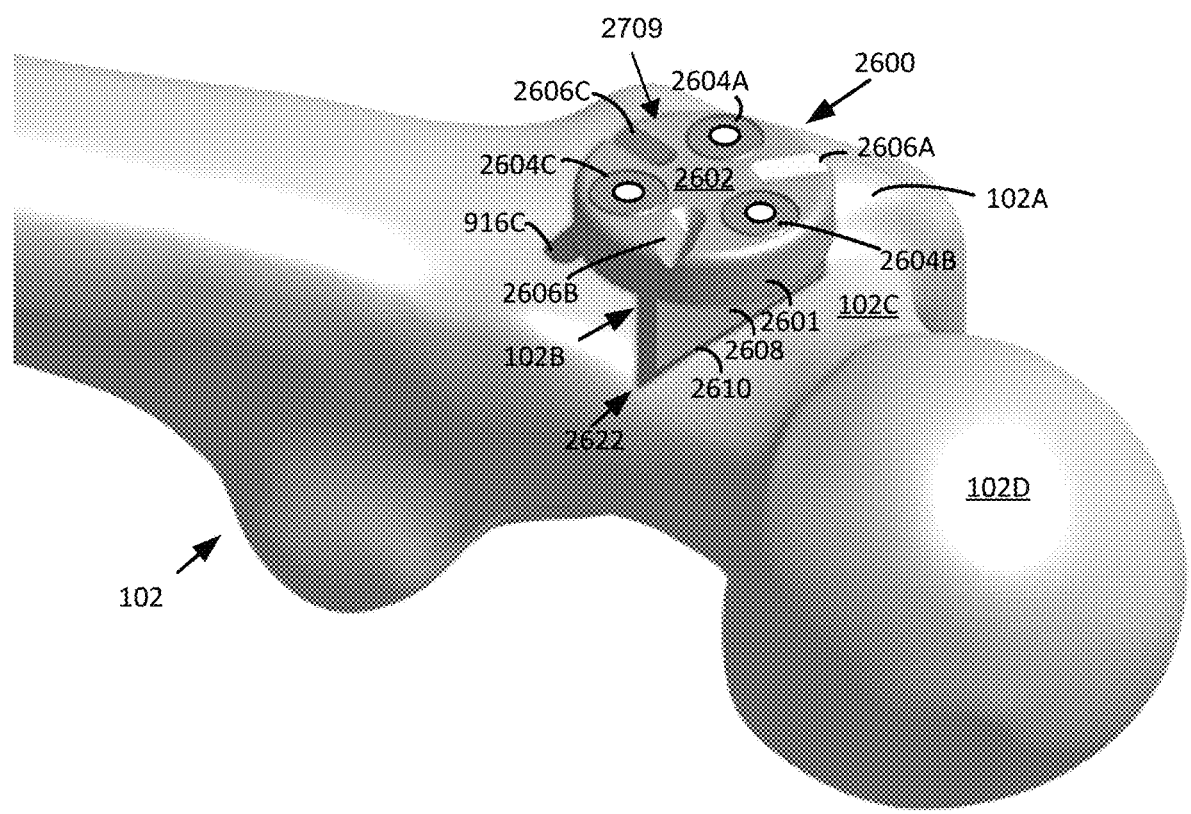
FIG. 27 is an illustration showing the neck resection guided platform of FIG. 26 coupled to the femur.
Figure 28:
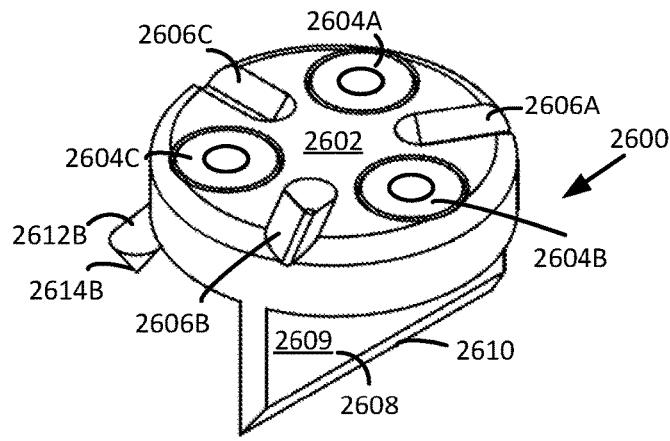
FIGS. 28, 29, 30 and 31 are respectively perspective, side, top and bottom views of the neck resection guided platform of FIG. 26 in isolation.

FIG. 26 is an illustration showing a perspective view of a tracker assembly 54 comprising a neck resection guided platform 2600, in accordance with an embodiment. Neck resection guided platform 2600 is shown mounted to a femur 102. Neck resection guided platform 2600 is further shown in assembly with a tracker 104 having a quick connect mechanism 106 for removable connection to the platform 2600. FIG. 27 is an illustration showing the neck resection guided platform 2600 mounted to the femur but without the tracker.

Figure 32:
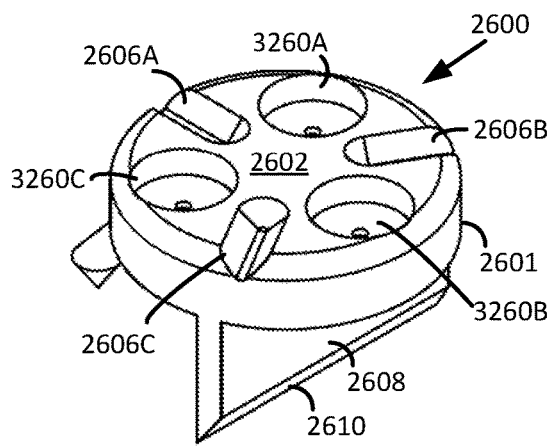
FIG. 32 is a perspective view of the neck resection guided platform of FIG. 28 without magnets.

FIGS. 28, 29, 30 and 31 are, respectively, perspective, side, top and bottom views of the neck resection guided platform 2600 in isolation. FIG. 32 is a perspective view of the neck resection guided platform 2600 shown without magnets.

Neck resection guided platform 2600 comprises a unitary body 2601 having an upper surface 2602 and an under surface 3100. From under surface 3100 extends a plurality of bone engaging projections as further described, while upper surface 2602 is configured to provide a tracker engaging interface 2709 for cooperatively coupling to quick connection mechanism 106. That is, upper surface 2602 is similar to upper surface 153 or 912 as previously described. Upper surface 2602 carries radially spaced magnets 2604A, 2604B and 2604C in three of the recesses defining magnet chambers 3200A, 3200B and 3200C. Interposed therebetween are three other recesses defining channels 2606A, 2606B and 2606C. The tracker engaging interface 2709 of the neck resection guided platform 2600 provides tracker removal and replacement features as previously described.

The plurality of bone engaging projections includes a cut engaging projection 2608, in the form of a blade shape, which eventually tapers toward its free end in a single-sided knife edge 2610. The shorter face 2609 of cut engaging projection 2608 faces outwardly relative to the platform 2600. Cut engaging projection 2608 extends across the width of platform 2600 just forward of a centre line 3102. Additional bone engaging projections include a pair of spaced and angled rear projections 2612A and 2612B that extend rearward (e.g. relative to the cut engaging projection 2608), and terminate in conical tips 2614A and 2614B. In the illustrated embodiment, the rear projections 2612A and 2612B extend beyond the dimension of the cooperative interface (e.g. its generally circular upper surface 2602). Respective support braces 2616A and 2616B extend from the under surface 3100 and connect a respective rear projection 2612A and 2612B to the cut engaging projection 2608. The support braces 2616A and 2616B extend a short distance and from the upper surface and are not bone engaging projections.

A further bone engaging projection comprises a generally centrally located marker projection 2018 that extends from the under surface 3100 and engages cut engaging projection 2608 in a perpendicular manner. Marker projection 2618 tapers toward a free end in a double knife edge 2620.

Figure 29:
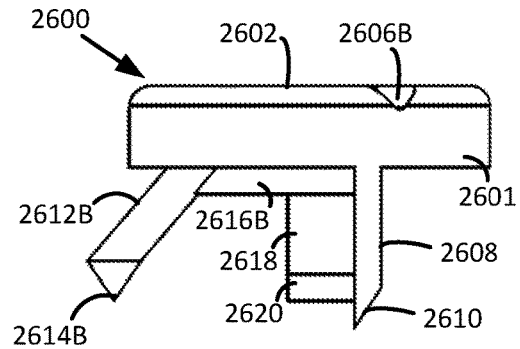
Figure 30:
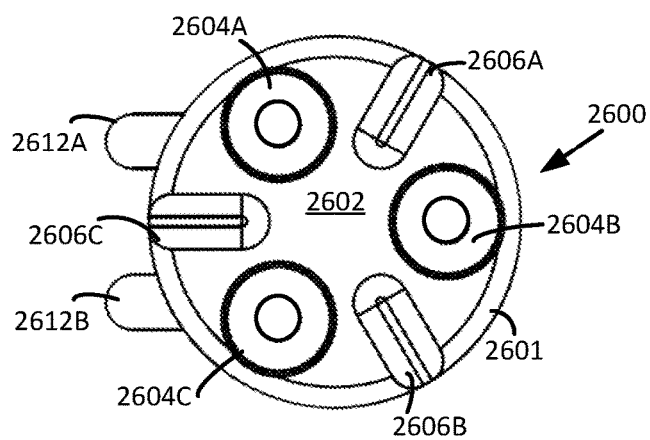
Figure 31:
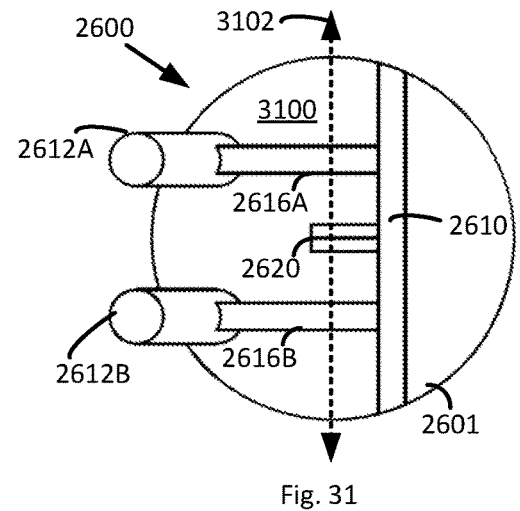

The plurality of bone engaging projections (e.g. 2608, 2612A, 2612B, and 2618) are configured (e.g. spaced and dimensioned) to provide stable support to the platform 2600 with a view to where the platform will be positioned on patient anatomy. The resection guided platform 2600 and its projections are configured to accommodate the contours of the bone, namely the femur about the greater trochanter 102A, the intertrochanteric line 102B, and the neck 102C. In particular, cut engaging projection 2608 is configured to position in a resection marking cut made in preparation of a final resection as further described. As illustrated in FIG. 29, cut engaging projection 2608 extends a greater distance from under surface 3100 than do the other bone engaging projections, for example by 2-3 mm, to fit within the marking cut.

Figure 33:
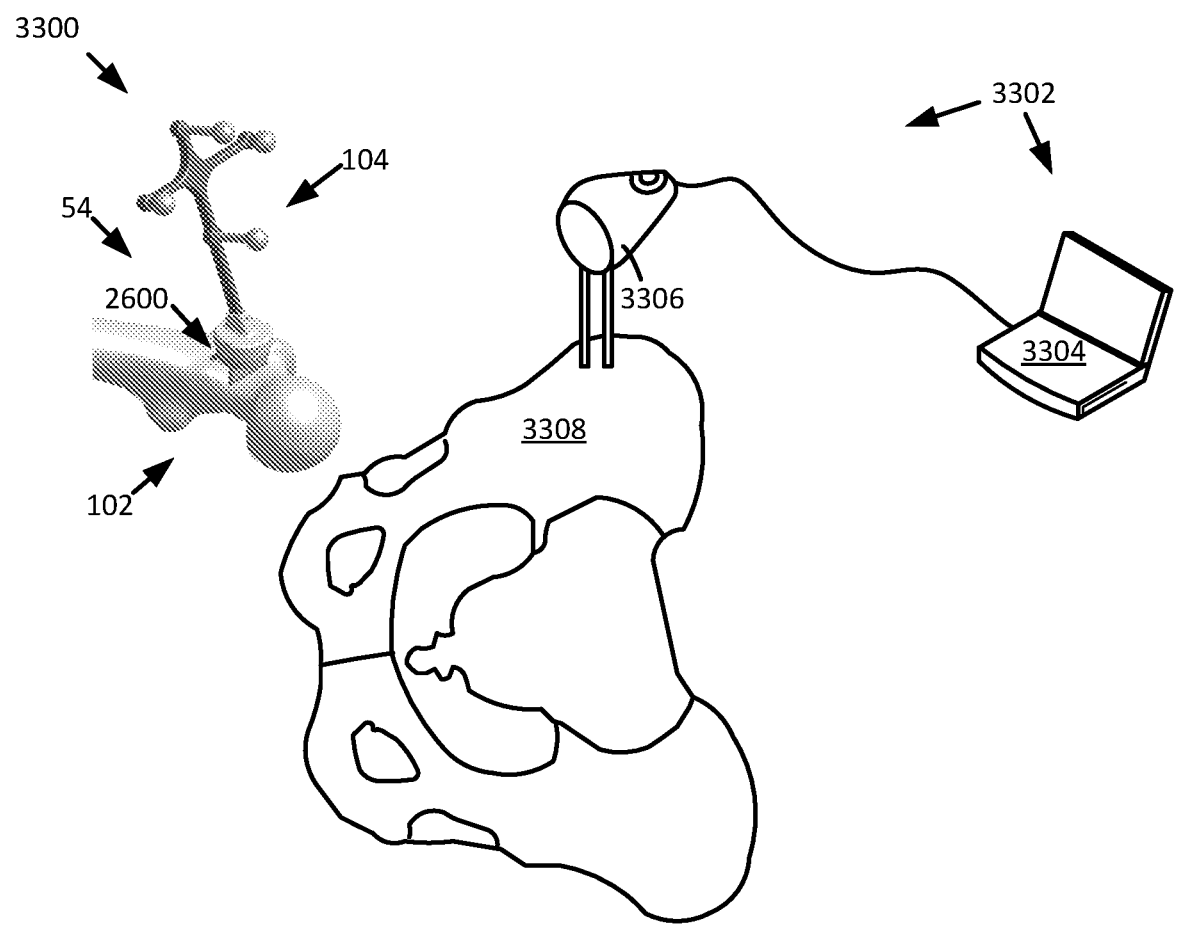
FIG. 33 is a representative computer assisted surgery system showing a localization system receiving optical information from a tracker assembly in accordance with an embodiment.

FIG. 33 is a representative computer assisted surgery system 3300 showing a localization system 3302 receiving optical information from a tracker assembly (e.g. representative assembly 54) in accordance with an embodiment for use with patient anatomy. In the embodiment, localization system 3302 comprises a computing device 3304 shown as a laptop but other form factors such as a personal computer, tablet, workstation, server, etc. are useful. Computing device 3304 comprises circuitry such as a processor and a storage device (e.g. memory), an input device, a display device and other output devices, etc. Computing device 3304 is coupled to an optical sensor 3306 comprising a camera, coupled to a pelvis in the present embodiment, to receive optical information in the form or passive or active light from the tracker 104. The camera could be mounted elsewhere as is known.

Tracker 104 forms part of tracker assembly 52 including platform 2600 and is coupled to a bone, in this case, femur 102. Though platform 2600 is shown, the tracker assembly 50 or 52 can be utilized with their respective platforms to provide tracking information (e.g. optical information from the tracker) to the computing device. In embodiments, computing device 3304 can be configured, such as via software (e.g. instructions stored that when executed by the processor configure the operation of the computing device 3304) to receive optical information and use it to generate guidance, a measurement or both. The optical information can be used in a registration operation performed by the localization system 3302 (e.g. invoked by a user thereof) to register an object (in this case a bone) to which the tracker assembly is attached. The object is registered to a coordinate system of the localization system 3302. Though not shown, the tracker 104 can be selectively attached to other objects such as a tool or implant for registration and tracking via localization system 3302. The localization system may execute an application that is specific to a particular procedure and can comprise workflow and other operations to guide the procedure and display measurements made using information from the tracker and the registration as is known.

In accordance with the teachings herein however, workflow and operations to generate various measurements can be configured to use target assembly 54 in a resection procedure. The workflow can be specific to the positioning and use of the platform 2600 relative to a resection cut to resect a femoral head as further described.

In use during a procedure to resect a femoral head 102D, an initial neck cut of only 2-3 mm is made where the surgeon intends to cut the neck later in surgical workflow. Localization workflow can guide the making of the preparatory cut, for example through a graphical user interface (GUI) via the display device. Auditory information can be provided and oral commands received via a microphone coupled to computing device 3304. Other user input can be received such as to advance or return through screens of the GUI, invoke capturing of optical information, perform various operations/calculations, etc.

The preparatory cut establishes a shallow line with the same width of the saw blade and kerf. Localization system workflow can guide the placement of the platform 2600. The GUI can guide the knife edge 2610 of the cut engaging projection 2608 to be placed into the resection line (e.g. 2622) so that it engages in and along the preparatory cut. The GUI can instruct that the platform be pressed into the bone so that the marker projection 2618 makes an impression (not shown) when the cut engaging projection is in the preparatory cut. The marker projection 2618 extends to engage the bone and its knife edge 2620 pierces the bone to provide a repeatable impression (e.g. a dimple or other shape) to return to when the platform 2600 is removed and replaced.

Using the preparatory cut 2622 and the impression, the user can place the tracker 104 on the resection guided platform 2600 and replace it into the same position on the femur 102 with high repeatability.

Figure 34:
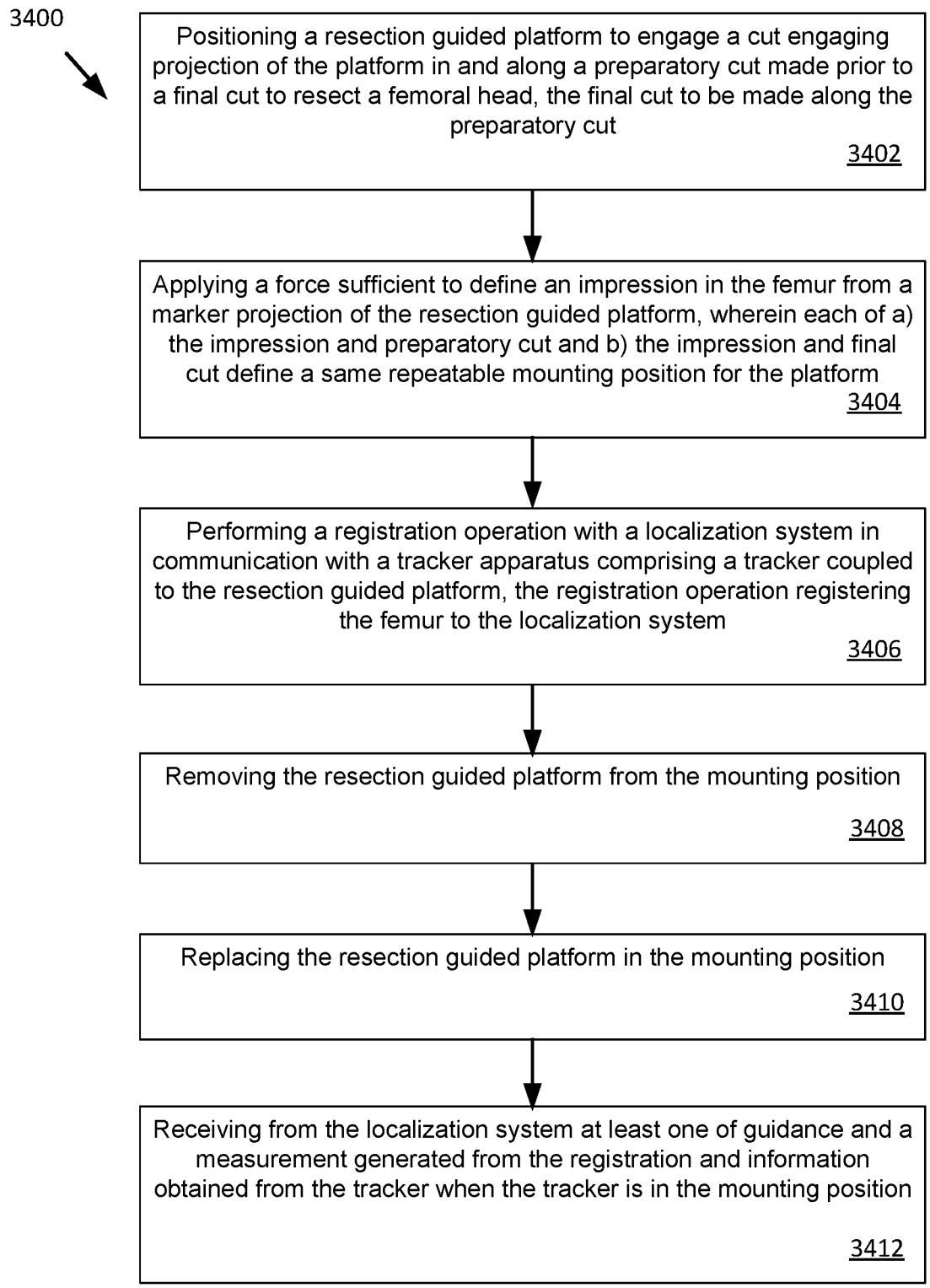

FIG. 34 is a flow chart of operations 3400 in accordance with an embodiment. Operations 3400 relate to mounting a platform 2600 to a bone 102. At step 3402, a resection guided platform is positioned to engage a cut engaging projection of the platform in and along a preparatory cut made prior to a final cut to resect a femoral head, the final cut to be made along the preparatory cut. At 3404, for example, with the cut engaging projection in and along the preparatory cut, a force is applied sufficient to define an impression in the femur from a marker projection of the resection guided platform. As such, each of a) the impression and preparatory cut and b) the impression and final cut define a same repeatable mounting position for the platform.

At 3406, for example, prior to performing the final resection and when the resection guided platform is in the same repeatable mounting position a registration operation is performed with a localization system in communication with a tracker apparatus comprising a tracker coupled to the resection guided platform. The registration operation registers the femur to the localization system.

For example, following the registration, at respectively 3408, 3410 and 3412, steps are performed to: remove the resection guided platform from the mounting position; replace the resection guided platform in the mounting position; and receive from the localization system at least one of guidance and a measurement generated from the registration and information obtained from the tracker when the tracker is in the mounting position. Steps 3402, 3404 and 3406 can define a first method to register the femur and steps 3408, 3410 and 3412 can define a second method to receive measurements and guidance following removal and replacement of the tracker.

A registration operation can be performed after the preparatory cut 2622 is made and with the tracker assembly 54 positioned on the bone as described. The tracker assembly can be removed and replaced without undergoing a second registration to receive guidance and measurements. That is, localization system 3302 can provide measurements and guidance using the same single registration for initial or subsequent placements of the tracker assembly 54 in a same position that was used for the same single registration. This is true even after the final cut is made as each of the i) impression and preparatory cut; and ii) the impression and the final cut define a same coupling position for the platform 2600. This approach assumes that the neck is completely resected, the final cut follows the same line as the preparatory cut 2622. The neck cut cannot be altered after the resection or the platform will not have sufficient contact points to return to the same position and orientation as used previously (during the registration).

FIG. 35 is a flowchart of operations 3500 in accordance with an embodiment. Operations 3500 can be performed by a localization system receiving tracker information from tracker assembly 54.

At 3502, operations register a bone to a localization system. The localization system is in communication with a tracker assembly comprising a tracker coupled to a resection guided platform and the resection guided platform is coupled to the bone to simultaneously engage: i) a cut engaging projection of the platform in and along a preparatory cut made prior to a final cut to resect a first portion of the bone, the final cut to be made along the preparatory cut; and ii) a marker projection of the platform in an impression in a second portion of the bone, the second portion remaining after the final cut, and the impression generated by the marker projection; and each of a) the impression and the preparatory cut and b) the impression and the final cut defining a same repeatable mounting position for the resection guided platform.

Following the registration: at steps 3504 and 3506, operations receive tracking information at the localization system from the tracker assembly when the tracker is coupled to the resection guided platform and the platform is in the same repeatable mounting position; and generate and present at least one of guidance and a measurement generated from the registration and the tracker information.

In an embodiment, tracking information is received after the final cut is performed and after the tracking assembly has been removed and subsequently replaced so that the platform is in the same repeatable mounting position; and the at least one of the guidance and the measurement are generated without performing a subsequent registration operation.

Though each of the platforms 100, 900 and 2600 are described as having kinematic interfaces to couple to a quick connect mechanism of a tracker, other cooperating interfaces can be utilised. Though use is described with reference to a femur, the platforms 100, 900 and 2600 can be configured for use with other bones, for example, configuring the shape and/or dimension of the bone engaging surfaces (including projections) accordingly. The length of the extension member of platforms 100 and 900 can be varied, etc. Though platform 2600 is described for use with a neck resection, the platform can be used for other resections. The platforms 100 and 900 are described with reference to a proximal member and a distal members connect via an extension member, using a femur placement as a reference. The proximal member faces a proximal end of the femur and the distal member extends toward a distal end of the femur. The proximal members of the respective platforms each form first end members and the distal members each form second end members.

The following clauses summarize some of the features of the resection guided platform and associated methods:

Clause 1. A resection guided platform for mounting a tracker to a bone, the platform comprising:
  a body having an upper surface and an under surface;
  the upper surface configured to provide a cooperative interface for coupling to the tracker; and
  the under surface configured to provide a plurality of platform projections extending from the upper surface, the projections comprising:
    a cut engaging projection configured for engaging in and along a preparatory cut in the bone, the preparatory cut made prior to a final cut to resect a portion of bone, the final cut to be made along the preparatory cut; and
    a marker projection comprising a surface for generating an impression in a portion of the bone to remain after the final cut, the impression to be generated when the cut engaging projection is in preparatory cut and a force is applied to the upper surface.

Clause 2. The platform of clause 1, wherein each of a) the impression and the preparatory cut and b) the impression and the final cut define a same repeatable mounting position for the resection guided platform.

Clause 3. The platform of clause 1 or 2, wherein the plurality of platform projections comprise at least one support projection configured to engage a bone surface of the bone to support the platform when coupled.

Clause 4. The platform of claim 3, wherein the support projection is angled or otherwise extends beyond a lateral periphery of the body.

Clause 5. The platform of any one of clauses 1 to 4, wherein the cut engaging projection extends to a position that is farther below the under surface than a position to which the marker projection extends.

Clause 6. The platform of claim 5, wherein the position to which the cut engaging projection extends is 2-3 mm farther than the position to which the marker position extends.

Clause 7. The platform of any one of clauses 1 to 6, wherein the marker projection is perpendicular to and engages the cut engaging projection.

Clause 8. The platform of any one of clauses 1 to 7, wherein marker projection tapers to a knife edge for generating the impression.

Clause 9. The platform of any one of clauses 1 to 8, wherein the cut projection defines a blade that extends along a width of the platform.

Clause 10. The platform of claim 8, wherein the cut projection tapers to a knife edge for engaging in and along the preparatory cut.

Clause 11. The platform of any one of clauses 1 to 10, wherein the body comprises a unitary body of a single piece of construction material.

Clause 12. The platform of any one of clauses 1 to 11, wherein the bone is a femur and the preparatory cut and final cut are for a femoral head resection.

Clause 13. A method comprising:
  registering a bone to a localization system, the localization system in communication with a tracker assembly comprising a tracker coupled to a resection guided platform and wherein:
    the resection guided platform is coupled to the bone to simultaneously engage:
      i) a cut engaging projection of the platform in and along a preparatory cut made prior to a final cut to resect a first portion of the bone, the final cut to be made along the preparatory cut; and
      ii) a marker projection of the platform in an impression in a second portion of the bone, the second portion remaining after the final cut, and the impression generated by the marker projection; and
    each of a) the impression and the preparatory cut and b) the impression and the final cut defining a same repeatable mounting position for the resection guided platform; and
  following the registration:
    receiving tracking information at the localization system from the tracker assembly when the tracker is coupled to the resection guided platform and the platform is in the same repeatable mounting position;
    generating and presenting at least one of guidance and a measurement generated from the registration and the tracker information.

Clause 14. The method of clause 13, wherein: the tracking information is received after the final cut is performed and after the tracking assembly has been removed and subsequently replaced so that the platform is in the same repeatable mounting position; and the at least one of the guidance and the measurement are generated without performing a subsequent registration operation.

Clause 15. A method comprising:
  positioning a resection guided platform to engage a cut engaging projection of the platform in and along a preparatory cut made prior to a final cut to resect a femoral head, the final cut to be made along the preparatory cut;
  with the cut engaging projection in and along the preparatory cut, applying a force sufficient to define an impression in the femur from a marker projection of the resection guided platform, wherein each of a) the impression and preparatory cut and b) the impression and final cut define a same repeatable mounting position for the platform;
  prior to performing the final resection and when the resection guided platform is in the same repeatable mounting position, performing a registration operation with a localization system in communication with a tracker apparatus comprising a tracker coupled to the resection guided platform, the registration operation registering the femur to the localization system;
  following the registration:
    removing the resection guided platform from the mounting position;
    replacing the resection guided platform in the mounting position; and
    receiving from the localization system at least one of guidance and a measurement
      generated from the registration and information obtained from the tracker when the tracker is in the mounting position.

Clause 16. The method of clause 15, wherein the at least one of the guidance and the measurement generated after the step of replacing are generated without performing a subsequent registration.

Clause 17. The method of clause 15 or 16 comprising, after the step of removing and before the step of replacing, performing the final resection to remove the femoral head.

Clause 18. The method of any one of clauses 15 to 17, wherein the step of positioning comprises applying pressure to one or more support projections of the platform to engage the support projections with a surface of the femur to support the platform thereon.

Clause 19. The method of any one of clauses 15 to 18, wherein the platform comprises a cooperating interface to couple with a quick connect mechanism of the tracker.

In addition to computing device aspects, a person of ordinary skill will understand that computer program product aspects are disclosed, where instructions are stored in a non-transient storage device (e.g. a memory, CD-ROM, DVD-ROM, disc, etc.) to configure a computing device to perform any of the method aspects stored herein.

Practical implementation may include any or all of the features described herein. For example components herein can be grouped and provided as a kit. A side mount kinematic platform 100 and a coupling base 108 can define a kit. A side mount kinematic platform 900 and a coupling base 1100 or 1800 can define a kit. Such a kit can further include an impactor tool 2000 for coupling base 1100 or 1800. These and other aspects, features and various combinations may be expressed as methods, apparatus, systems, means for performing functions, program products, and in other ways, combining the features described herein. A number of embodiments have been described.

Nevertheless, it will be understood that various modifications can be made without departing from the spirit and scope of the processes and techniques described herein. In addition, other steps can be provided, or steps can be eliminated, from the described process, and other components can be added to, or removed from, the described systems. Accordingly, other embodiments are within the scope of the following claims.

Throughout the description and claims of this specification, the word "comprise" and "contain" and variations of them mean "including but not limited to" and they are not intended to (and do not) exclude other components, integers or steps. Throughout this specification, the singular encompasses the plural unless the context requires otherwise. In particular, where the indefinite article is used, the specification is to be understood as contemplating plurality as well as singularity, unless the context requires otherwise.

Features, integers characteristics, compounds, chemical moieties or groups described in conjunction with a particular aspect, embodiment or example of the invention are to be understood to be applicable to any other aspect, embodiment or example unless incompatible therewith. All of the features disclosed herein (including any accompanying claims, abstract and drawings), and/or all of the steps of any method or process so disclosed, may be combined in any combination, except combinations where at least some of such features and/or steps are mutually exclusive. The invention is not restricted to the details of any foregoing examples or embodiments. The invention extends to any novel one, or any novel combination, of the features disclosed in this specification (including any accompanying claims, abstract and drawings) or to any novel one, or any novel combination, of the steps of any method or process disclosed.

What is claimed is:

1. A side mount platform to mount a tracker to a bone via a coupling base, the platform comprising:
a body having a first end member and a second end member laterally connected to and spaced from the first end member by an extension member of the body;
wherein the first end member comprises an under surface providing a base coupling interface for coupling to the coupling base;
wherein the second end member comprises an upper surface providing a tracker coupling interface for coupling the platform to the tracker;
wherein the extension member is angled such that a plane occupied by an upper surface of the first end member is different from a plane occupied by the upper surface of the second end member; and
wherein an under surface of the extension member and an under surface of the second end member are configured to follow a contour along a portion of the bone over which the extension member and the second end member are to be placed.

2. The platform of claim 1, wherein the tracker coupling interface comprises a cooperative interface for coupling to a quick connect mechanism of the tracker.

3. The platform of claim 1, wherein the tracker coupling interface is magnetic.

4. The platform of claim 1, wherein the first end defines at least one recess for the base coupling interface to receive a portion of the coupling base.

5. The platform of claim 1, wherein the first end defines at least one projection for base coupling interface to fit a cooperating recess of the coupling base.

6. The platform of claim 1, wherein the first end defines a recess for the base coupling interface to receive a cooperating projection of the coupling base for guiding a lateral coupling of the platform and coupling base.

7. The platform of claim 1, wherein the base coupling interface comprises at least one magnet to couple with the coupling base.

8. The platform of claim 7, wherein each of the at least one magnet is positioned on the first end to mate with a cooperating magnet of the coupling base.

9. The platform of claim 1, wherein the base coupling interface constrains movement of the platform in 6 degrees of freedom when coupled to the coupling base.

10. The platform of claim 1, wherein the base coupling interface constrains movement of the platform in 5 degrees of freedom when coupled to the coupling base, the base coupling interface permitting rotation of the platform about an axis of the coupling base.

11. The platform of claim 1, wherein the platform is a component of an assembly comprising the coupling base.

12. The platform of claim 11, wherein the coupling base comprises one of: a staple and a pair of pegs.

13. The platform of claim 11, wherein the coupling base comprises a base body having a bone engaging surface and an opposing surface; the opposing surface providing a cooperative interface to engage the bone coupling interface of the platform.

14. The platform of claim 13 wherein the base body defines an aperture therethrough extending between the opposing surface and the bone engaging surface to receive a fastener for coupling the base body to a coupling portion of the bone.

15. The platform of claim 14, wherein the aperture is angled from normal to direct the fastener.

16. A side mount platform to mount a tracker to a bone via a coupling base, the platform comprising:
a body having a first end member and a second end member laterally connected to and spaced from the first end member by an extension member of the body;
wherein the first end member comprises an under surface providing a base coupling interface for coupling to the coupling base;
wherein the second end member comprises an upper surface providing a tracker coupling interface for coupling the platform to the tracker;
wherein the first end defines a recess for the base coupling interface to receive a cooperating projection of the coupling base for guiding a lateral coupling of the platform and coupling base; and
wherein the recess is Y-shaped.

17. The platform of claim 16, wherein the extension member is angled such that a plane occupied by an upper surface of the first end member is different from a plane occupied by the upper surface of the second end member.

18. A side mount platform to mount a tracker to a bone via a coupling base, the platform comprising:
a body having a first end member and a second end member laterally connected to and spaced from the first end member by an extension member of the body;
wherein the first end member comprises an under surface providing a base coupling interface for coupling to the coupling base; and
wherein the second end member comprises an upper surface providing a tracker coupling interface for coupling the platform to the tracker;
wherein the base coupling interface constrains movement of the platform in 5 degrees of freedom when coupled to the coupling base, the base coupling interface permitting rotation of the platform about an axis of the coupling base; and
wherein the base coupling interface comprises a pair of magnets coupled with a ferrous coupler, the magnets deposed over a pair of recesses configured to receive spherical projections of the coupling base.

19. The platform of claim 18, wherein one of the pair of recesses comprises a socket and the other a channel.

20. A side mount platform to mount a tracker to a bone via a coupling base, the platform comprising:
a body having a first end member and a second end member laterally connected to and spaced from the first end member by an extension member of the body;
wherein the first end member comprises an under surface providing a base coupling interface for coupling to the coupling base;
wherein the second end member comprises an upper surface providing a tracker coupling interface for coupling the platform to the tracker;
wherein the base coupling interface constrains movement of the platform in 5 degrees of freedom when coupled to the coupling base, the base coupling interface permitting rotation of the platform about an axis of the coupling base; and wherein the second end member comprises an under surface having a bone engaging projection, to engage a portion of the bone to stop rotation about the axis.

21. A side mount platform to mount a tracker to a bone via a coupling base, the platform comprising:
- a body having a first end member and a second end member laterally connected to and spaced from the first end member by an extension member of the body;
- wherein the first end member comprises an under surface providing a base coupling interface for coupling to the coupling base;
- wherein the second end member comprises an upper surface providing a tracker coupling interface for coupling the platform to the tracker:
- wherein the platform is a component of an assembly comprising the coupling base;
- wherein the coupling base comprises one of: a staple and a pair of pegs; and
- wherein each of the staple and the pair of pegs comprises a pair of spherical tips to engage a pair of recesses of the base coupling interface in the under surface of the first end.

* * * * *